United States Patent
O'brien et al.

(10) Patent No.: US 12,324,624 B2
(45) Date of Patent: Jun. 10, 2025

(54) GLARE TESTING DEVICE

(71) Applicant: The Government of the United States, as Represented by the Secretary of the Army, Fort Detrick, MD (US)

(72) Inventors: Kevin John O'brien, Fort Rucker, AL (US); Victor Alan Estes, Fort Rucker, AL (US)

(73) Assignee: The Government of the United States, as Represented by the Secretary of the Army, Ft. Detrick, MD (US)

( * ) Notice: Subject to any disclaimer, the term of this patent is extended or adjusted under 35 U.S.C. 154(b) by 780 days.

(21) Appl. No.: 17/432,007

(22) PCT Filed: Feb. 21, 2020

(86) PCT No.: PCT/US2020/019303
§ 371 (c)(1),
(2) Date: Aug. 18, 2021

(87) PCT Pub. No.: WO2020/172582
PCT Pub. Date: Aug. 27, 2020

(65) Prior Publication Data
US 2023/0000339 A1  Jan. 5, 2023

Related U.S. Application Data

(60) Provisional application No. 62/808,963, filed on Feb. 22, 2019.

(51) Int. Cl.
A61B 3/032 (2006.01)
A61B 3/06 (2006.01)

(52) U.S. Cl.
CPC .............. *A61B 3/032* (2013.01); *A61B 3/063* (2013.01)

(58) Field of Classification Search
CPC ................................ A61B 3/032; A61B 3/063
USPC .......................................................... 351/243
See application file for complete search history.

(56) References Cited

U.S. PATENT DOCUMENTS

| | | | |
|---|---|---|---|
| 2,321,915 A | 6/1943 | Higley | |
| 5,592,247 A * | 1/1997 | Trokel | A61B 3/06 351/239 |
| 5,969,792 A * | 10/1999 | Ginsburg | A61B 3/063 351/243 |
| 6,099,126 A * | 8/2000 | Teskey | A61B 3/06 351/213 |
| 2002/0047997 A1* | 4/2002 | Hayashi | A61B 3/022 351/239 |
| 2009/0150372 A1* | 6/2009 | Batista Reyes | G06F 16/951 707/999.005 |
| 2010/0265463 A1* | 10/2010 | Lai | A61B 3/0285 351/237 |
| 2012/0162606 A1 | 6/2012 | Nakamura et al. | |
| 2012/0249960 A1* | 10/2012 | Plaian | A61B 3/14 351/221 |

(Continued)

OTHER PUBLICATIONS

International Search Report for International Patent Application No. PCT/US20/19303 dated Jun. 25, 2020.

*Primary Examiner* — Sharrief I Broome
(74) *Attorney, Agent, or Firm* — Leigh Z. Callander

(57) ABSTRACT

A glare source device, a glare test system and methods that assesses visual performance and discomfort under varying levels of glare under varying lighting conditions is provided.

12 Claims, 39 Drawing Sheets

(56) References Cited

U.S. PATENT DOCUMENTS

2014/0209254 A1* 7/2014 Birru .................. E06B 9/68
  160/5
2015/0313458 A1* 11/2015 Butler ................ A61B 3/0008
  351/243

* cited by examiner

Display Area: 4.3" x 2.6"

60 Hz Refresh Rate 800 x 480 pixels => 186 ppi

~1Khz PWM signal recommended @ 3-5V logic screen is detachable from controller

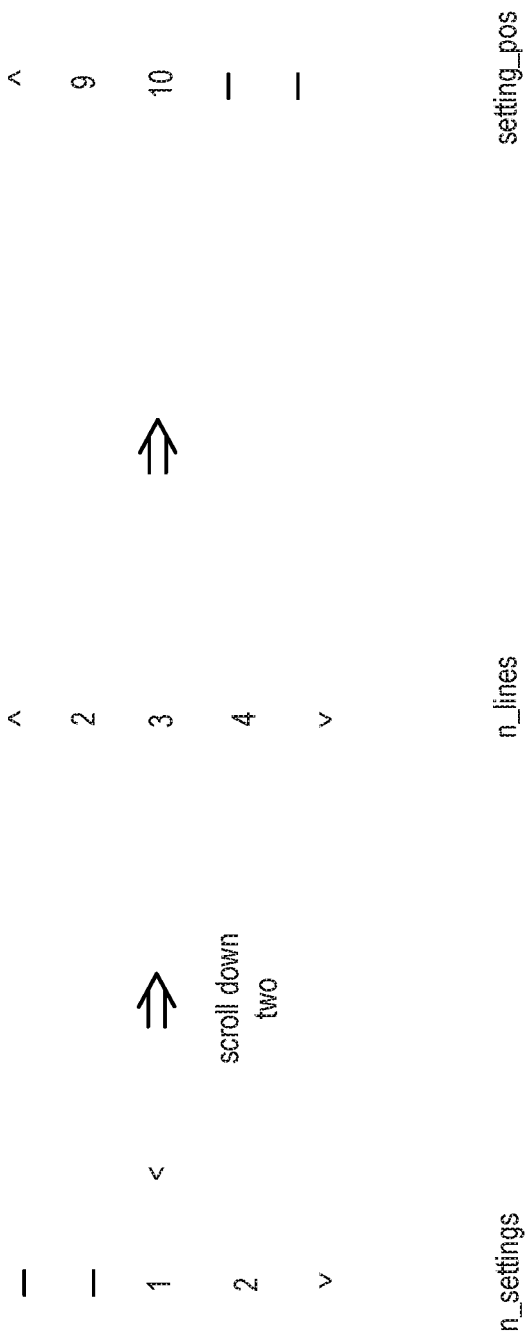

GLARE TESTING DEVICE

CROSS-REFERENCE TO RELATED APPLICATIONS

This application is the National Stage entry of International Application No. PCT/US20/19303, filed Feb. 21, 2020, which claims the benefit of United States Provisional Application No. 62/808,963, filed Feb. 22, 2019, the contents of which are hereby incorporated by reference in their entirety.

STATEMENT AS TO RIGHTS OR INVENTIONS MADE UNDER FEDERALLY SPONSORED RESEARCH AND DEVELOPMENT

This invention was made with government support from the Aeromedical Research Laboratory, a subordinate organization of the United States Army Medical Research and Materiel Command and Oak Ridge Institute of Science and Education, a subordinate organization of the United States Department of Energy. The United States Government has certain rights in the invention.

FIELD OF THE INVENTION

Materials, apparatus, methods, and systems for vision testing.

DESCRIPTION OF RELATED ART

Glare, whether from sunlight or artificial light sources, is a ubiquitous issue for vehicle operators.

The issues presented by glare for aviators are even greater than those experienced by terrestrial vehicle operators, due to increased elevation, reduced atmospheric filtering, a greater need for situational awareness, higher velocities (resulting in reduced time windows), and the requirement to maintain specific aircraft orientations or flight corridors. Corneal surgeries (such as Lasik, PRK, etc) often create greater glare sensitivity as a side effect in aviators involved in military aviation.

Visual acuity of a patient measured in a standard dark refracting lane in an ophthalmologist's or optometrist's office may not be indicative of the patient's acuity in bright light or glare conditions. Particularly, this is so, if the patient suffers from eye disorders such as cataracts or corneal scarring. In order to provide a more thorough assessment of a patient's visual acuity, brightness acuity or "glare" testers have been devised. However, most commercially available glare disability assessment devices are intended to only create a binary PASS/FAIL metric of visual performance in clinical patients with suspected cataracts and are not intended to identify the performance limits of healthy adults. Other disadvantages of current systems include commercially available systems for assessment of glare disability typically have either one or a very small number of available intensities. The VectorVision CV-1000 system has a single intensity level, the Brightness Acuity Tester has only three intensity levels, and the EpiGlare system also has only three intensity levels. These devices lack varying intensity levels and fail to identify performance limits in health adults. Accordingly, a need exists for a simple device and method for glare testing that assesses visual performance and discomfort under varying levels of glare and varying lighting conditions.

SUMMARY OF THE INVENTION

The present invention provides a glare testing device and methods that assess visual performance and discomfort under varying levels of veiling glare under photopic and mesopic light conditions. A glare testing device and methods that assesses visual performance and discomfort under varying levels of veiling glare under photopic and mesopic light conditions have been invented. A further embodiment is an electronic device/system for producing the varying levels of glaring light. Furthermore, the subject disclosure presents systems and methods for calculating visual performance and discomfort under varying levels of veiling glare under photopic and mesopic light conditions.

BRIEF DESCRIPTION OF THE DRAWINGS

The following drawings form part of the present specification and are included to further demonstrate certain embodiments of the present invention. The invention may be better understood by reference to one or more of these drawings in combination with the detailed description of specific embodiments presented herein.

FIG. 3(A)-(C) is a schematic illustrating component parts in a glare source and identification of appropriate MOSFET for switching LEDS in certain embodiments. (A) shows a microcontroller connected to an LED driver integrated circuit which is used to drive a MOSFET (metal-oxide semi-conductor field-effect transistor) that switches on and off a set of LEDs connected in parallel. (B) shows a microcontroller connected to an LED driver controlling a set of LEDs in parallel using a transistor. Additionally, it contains intended connections for a hex debouncing integrated circuit, logical connections for supply power and ground through standard micro-USB pinouts, and a trio of decoupling capacitors for maintaining the stability of integrated circuits. (C) shows a conception of a settings menu for the device intended to be operable with a knob and buttons rather than a keyboard or mouse.

KEY FOR LABELLED PARTS FOR THE FIGURES

Figures 1A, 1B:
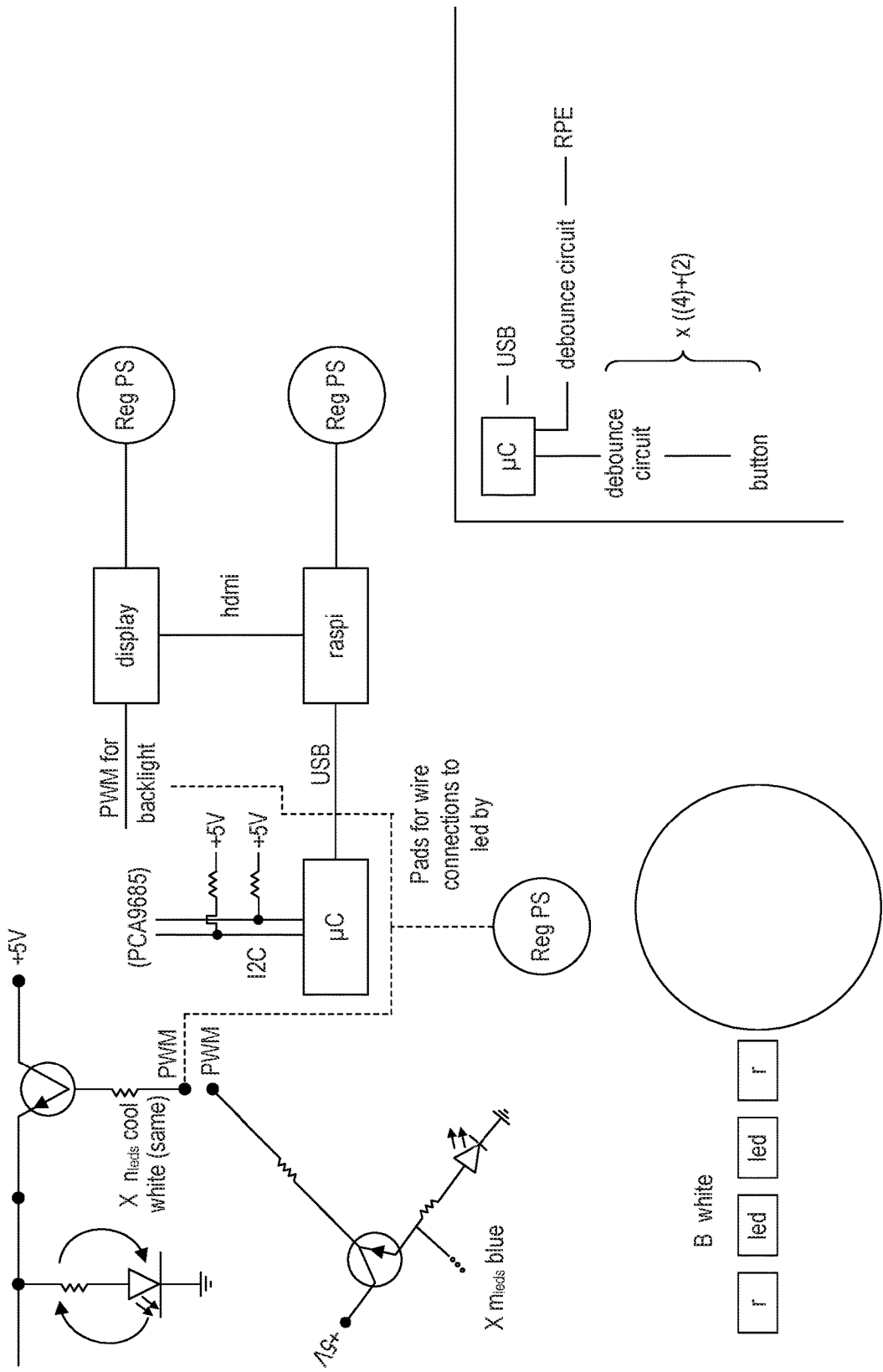
FIGS. 1(A) and (B) are block diagrams illustrating (A) connections between a display, a micro-computer, a micro-controller, and LEDS for a glare source and (B) an input device in certain embodiments.

Schematic Parts/Key for Labelled Parts of FIGS. 4, 5, 7, 9, 10, and 12:
A. Current limiting resistors for LEDs
B. LEDs
C. Switching transistor (MOSFET)
D. Resistor for switching transistor
E. Terminal block
F. Decoupling capacitor (full board)
G. Address resistors
H. LED driver chip
I. Decoupling capacitors for LED driver chip
J. Micro USB power connector
K. Pull-up resistors for $I^2C$ connection
L. Microcontroller
M. Button
N. Decoupling capacitor for hex bounce eliminator
O. Hex bounce eliminator
P. Oscillation capacitor for hex bounce eliminator
Q. Rotary encoder
R. Hole in PCB for viewing
S. Mounting hole Schematic/Key for Labelled Parts of FIGS. 24-31:
A. DIP switches for assigning addresses to LED driver chips
B. Pull-down resistors for DIP switch
C. Per-LED smoothing capacitors
D. LEDs
E. Current limiting resistors for LEDs
F. LED driver chip
G. Decoupling capacitors for LED driver chip
H. Large capacitor for decoupling entire board
I. Connector (micro-USB) for $I^2C$ data line and power
1. Mounting hole
2. Pads for full-board decoupling capacitor
3. Pads for 6-positon DIP switch
4. Resistors for DIP switch
5. Structural pads for micro-USB connector
6. Decoupling capacitors for LED driver
7. Pads for LED driver
8. Pads for smoothing capacitors for LEDs
9. Resistors to limit current to LEDs
10. LEDs
11. Void in copper layer for physical hole in circuit board
12. Electrical and structural pads for micro-USB connector.

In the Summary above, in the Detailed Description below, and the claims below, as well as the accompanying figures, reference is made to particular features of the invention. It is to be understood that the disclosure of the invention in this specification does not includes all possible combinations of such particular features. For example, where a particular feature is disclosed in the context of a particular embodiment or embodiment of the invention, or a particular claim, that feature can also be used, to the extent possible, in combination with and/or in the context of other particular embodiments and embodiments of the invention, and in the invention generally. For the purposes of explanation, numerous specific details are set forth in order to provide a thorough understanding of the present invention. It will be apparent, however, to one skilled in the art that the present invention may be practiced without these specific details.

DETAILED DESCRIPTION

The invention provides an electronic device/system for producing varying levels of glaring light which interferes with vision. The electronic device generates light to produce visual glare for a test subject (glare source). The electronic device which generates the glare source is suitable for glare disability testing which can be used to simulate directional glare sources which move across the visual field or are indications of different lighting conditions. In an embodiment, the device allows for precise quantification of effects of glare, such as decreases in visual performance or increases in discomfort, in for example, a glare testing device.

The majority of commercially available glare testing equipment offers few options for intensity and little to no flexibility in changing the angular orientation of glare. The current clinically available options are intended primarily for assessing a pass-fail criteria for minimum visual performance in mostly elderly and pathology-related populations, while the instant device has sufficient intensity to assess performance in young, health subjects, can be dimmed low enough to provide glare in low-light conditions, and can be adjusted rapidly and precisely enough to permit changes in the glare to satisfy a perceptual criteria (or a performance criteria can be tested with a static setting as is traditional in clinical assessments).

In an embodiment, the electronic device comprises LEDs mounted to a circuit board and also comprises an opening. In an embodiment, the opening can be either within the circuit board or between two or more circuit boards. In an embodiment, the opening can be in the shape of a slit or a circle, or any preferred shape depending on the desired optical geometry. In an embodiment, the LEDs can be in any shape (i.e., square, rectangle, etc) design depending on desired optical geometry/arrangement of LEDs. For example, the electronic device can comprise a ring of LEDs mounted to a circuit board, comprising a circular opening in the center (FIGS. 3, 10-13, 25-31). The electronic device can also comprise 2 linear arrays of LEDs mounted on a circuit board, with an opening/gap between the arrays. In an aspect, the linear arrays arrangement maintains the peripheral field of view.

Figure 32:
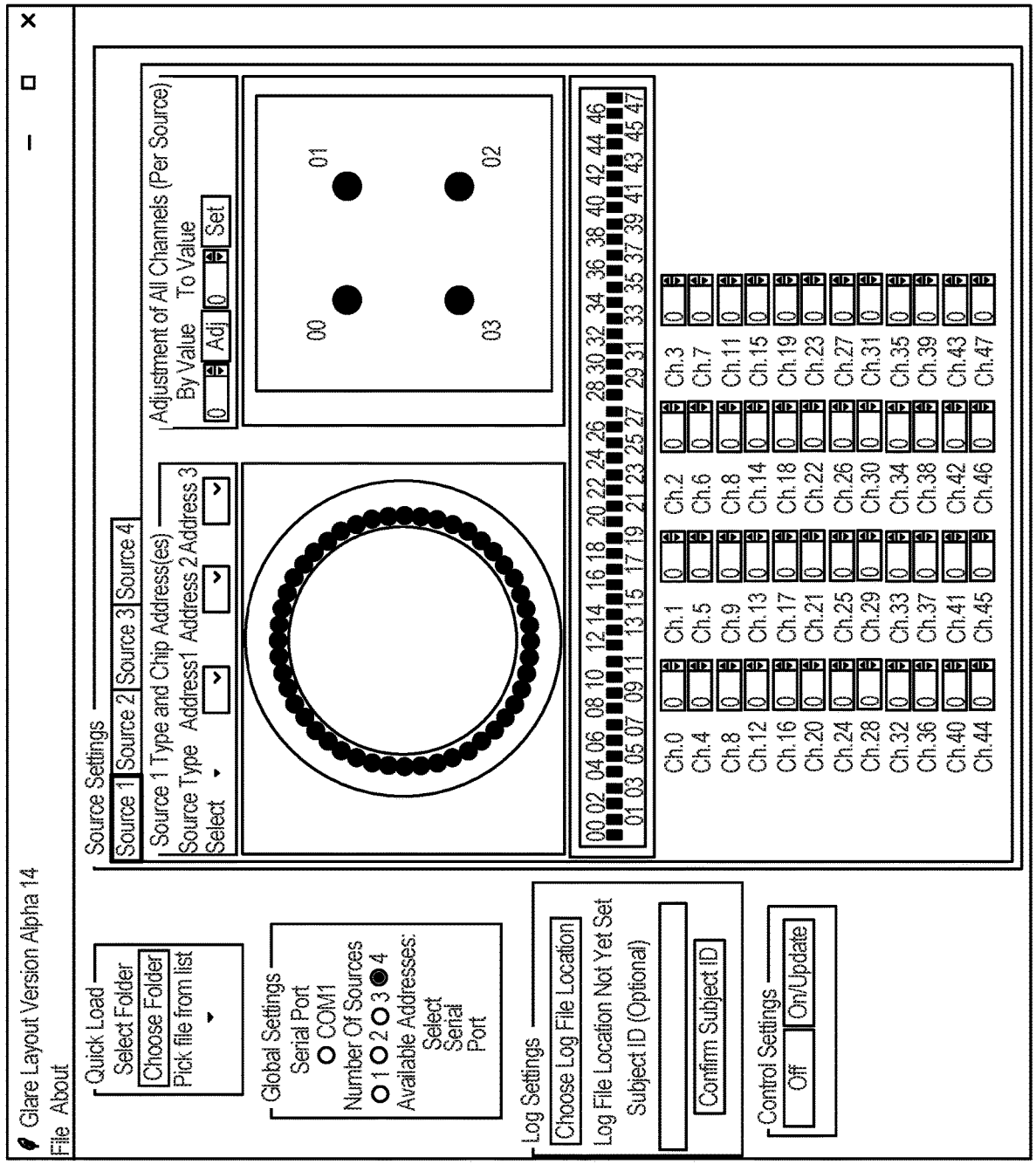
FIG. 32 is a screenshot of the associated software with the circuit board/device and illustrates that each LED is individually controllable.

In an embodiment, the LEDs can be tied together with a single transistor, with a single output channel, wherein the LEDs are all tied/controlled together by a single signal. In this embodiment, all the LEDs are set to an identical brightness level. If the geometry of the LEDs permit, such an embodiment can result in a symmetric homogeneous glare. In another embodiment, the LEDs are individually independently controlled so each LED can be set to a different brightness level (FIGS. 24 and 32). Such an embodiment results in an asymmetric heterogeneous glare, which is more representative of natural lighting conditions or common artificial lighting conditions. In another embodiment, there are 2 separate parallel controllers, wherein the LEDs can be either tied together with a single resistor with a single output channel, or individually independently controlled, depending on preference.

In an embodiment, the electronic device comprises at least 3 LEDs, 10 LEDs, 20 LEDs, 40 LEDs, 48 LEDs, 60 LEDs, 80 LEDs, 100 LEDs, 150 LEDs, 200, LEDs, 300 LEDs, 500 LEDs, 1000 LEDs, etc. In an embodiment, the number of LEDs present on the electronic device is limited only by the desired geometry and fit of the LEDs onto the circuit board. In an embodiment, there are at least 48 LEDs.

Figure 2:
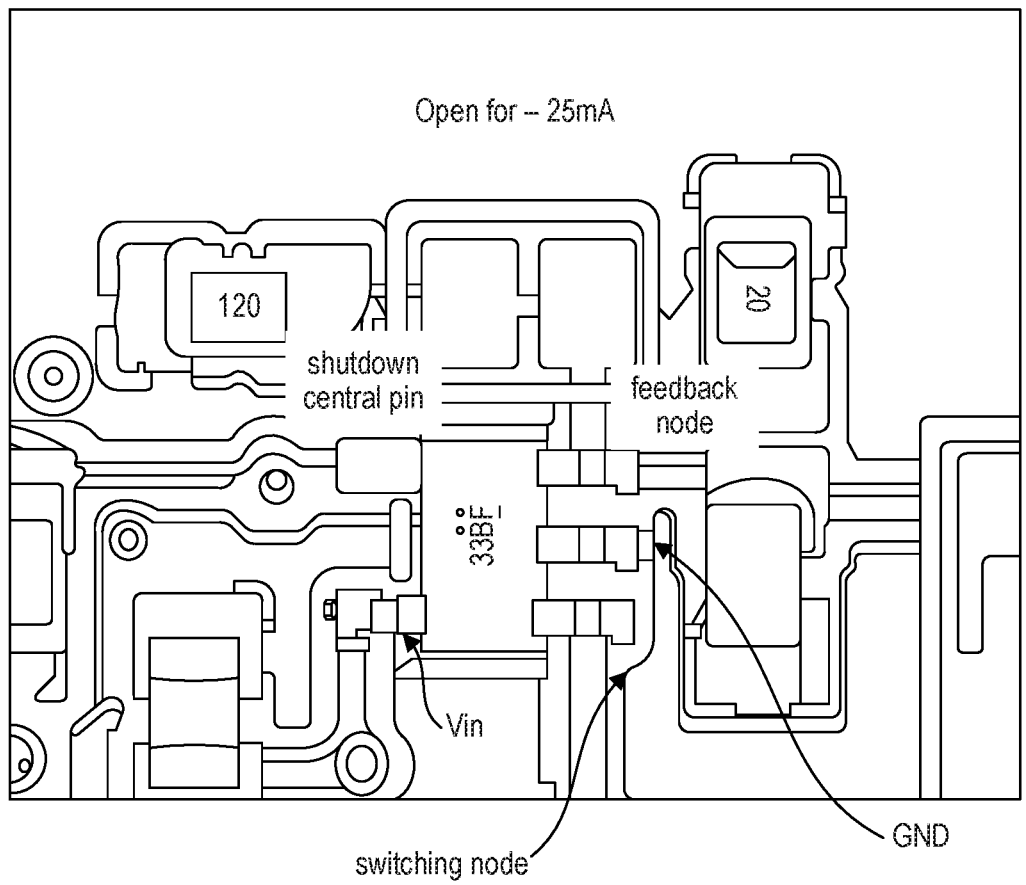
FIG. 2 is an illustration of a section of a manufacturer's display in certain embodiments.
Figure 3A:
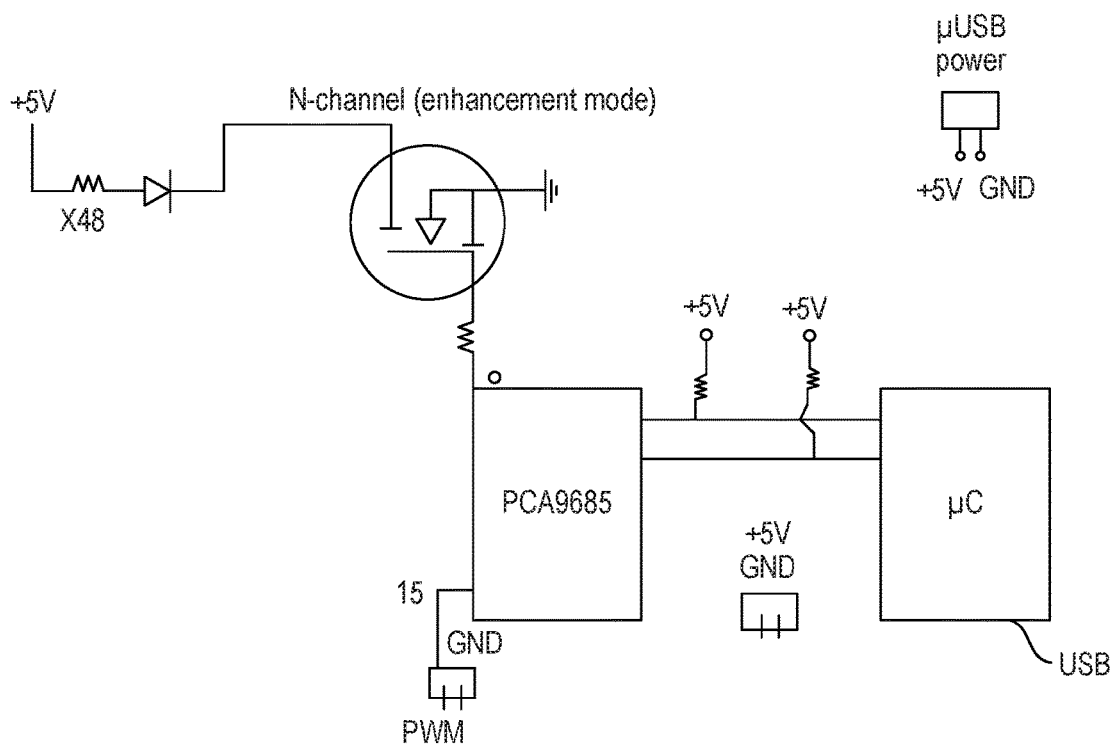
Figure 3A:
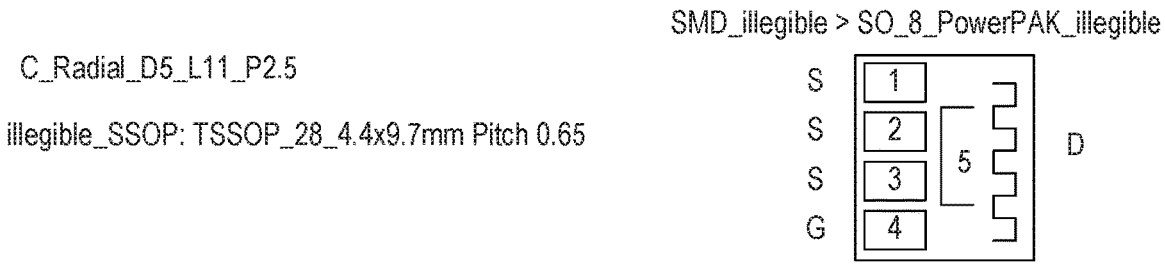
Figure 3B:
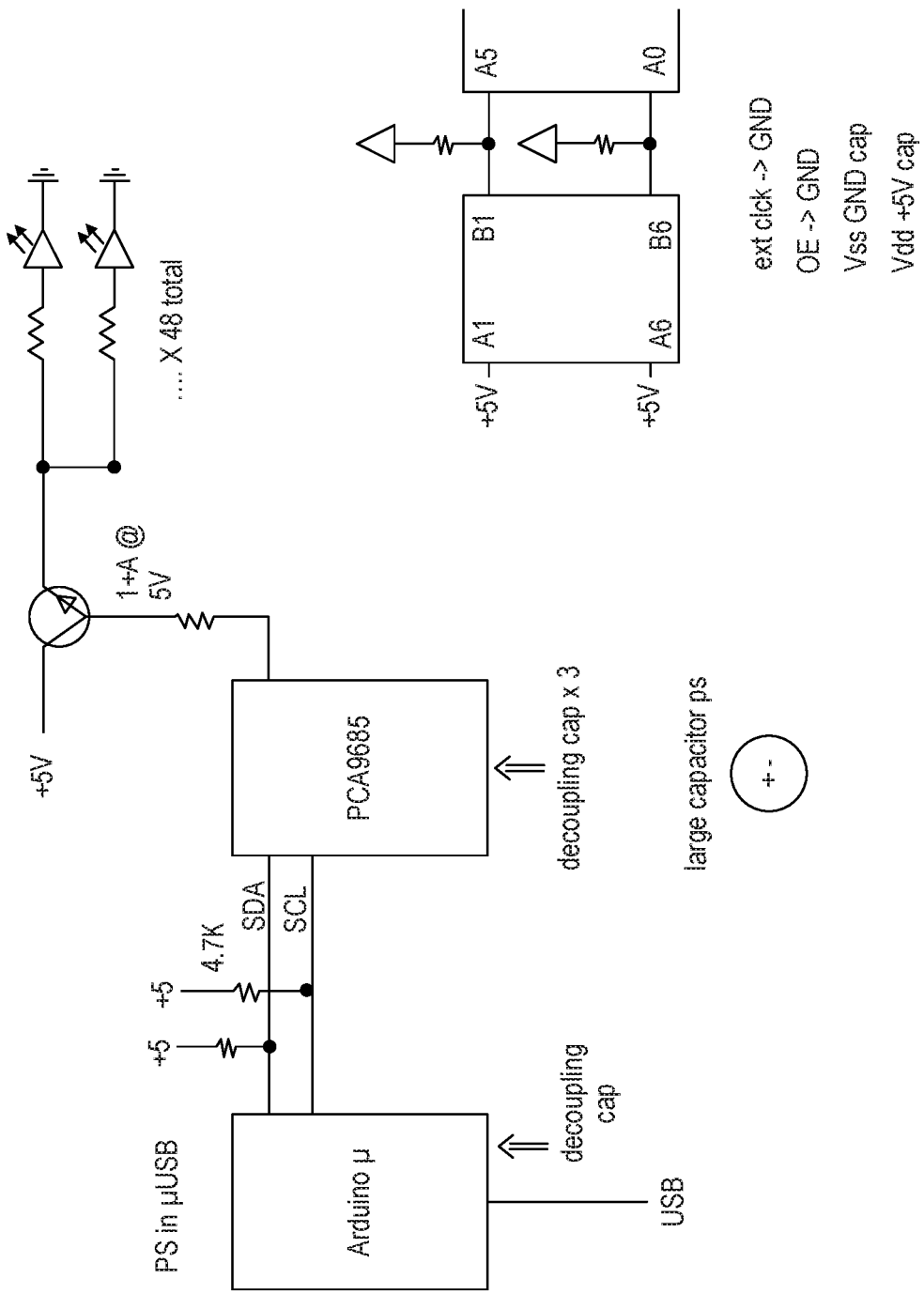

In an embodiment, the assembled circuit board (FIGS. 10-15, and 25-31) is mounted or held near a test subject's eye, the test subject looks through the opening in the electronic device, and various combination of the LEDs on the board are used to generate glare. When the LEDs are turned on, visibility is reduced because of the resulting glare. The brightness of each LED is controlled via pulse width modulation (PWM), and each LED can be set to any one of many different brightness levels, depending on the bit depth of the LED driver used. (PWM can be used to switch an LED on and off very rapidly to achieve different bright levels) (FIGS. 2 and 32).

The number of possible brightness levels per LED is calculated according to:
$2^{\wedge LED\ driver\ bit\ depth}$.

For example, the number of different brightness levels for a 12-bit depth LED driver is 4096. A 10-bit depth LED driver would have 1024 levels, and a 16-bit depth LED driver would have 65536.

The number of different brightness level for total number of LED's is calculated according to:
$(2^{\wedge LED\ driver\ bit\ depth})^{\wedge (number\ of\ LEDs)}$.

For example, for a ring of 48 LEDs, the number of different brightness levels is $2.47*(10^{\wedge}173)$ $((4096^{\wedge}48)$ which is $((2^{\wedge}12)^{\wedge}48)$.

In an embodiment, the LEDs have increased amounts of shorter wavelengths, which is better able to mimic natural sunlight or common artificial light sources and can contribute more to visual glare compared to longer wavelengths. The halogen or incandescent lamps historically used in clinical glare testing equipment have relatively little light output in the 400 nanometer to 500 nanometer wavelength range. Cool white LEDs typically have much more of their energy in the 400 nm-500 nm range, and as a result do a better job of approximating sunlight for glare-related applications. In an embodiment, the LEDs are cool white LEDs.

In an embodiment, the board receives power and a data signal (using the common I²C protocol) through a cable and is controlled using a custom-built user interface. In an embodiment, when a signal is transmitted through the user interface, there is a serial connection to a microcontroller and a cable to LED source band, the LED drivers interpret the signal transmitted by a microcontroller and adjust the LED intensity (via PWM, which can turn the digital source on/off). In another embodiment, an alternative means of driving the microcontroller is used, i.e., Bluetooth or an internet enabled signal: control software→computer (or other device running the software)→microcontroller→LED driver→LEDs.

An important aspect of the device, which separates it from other commercially available devices, is very fine brightness adjustment (i.e., typical available devices only has two or three bright settings, including "off", but in contrast, the device has a much greater number of brightness levels per LED) and fine radial adjustments. As a result, there are many unique lighting conditions which can be created with the devices (2^LED driver bit depth) A (number of LEDs). With this capability, glare can be adjusted in intensity and geometry allowing for better replication of environmental glare phenomena, i.e., glare can be made to come from precise directions to emulate oncoming headlights, sunlight at different types of day, or other directional sources of glare. The angular adjustment and number of brightness levels appear to both dwarf anything currently on the market. Additionally, another embodiment staggers the LEDs on and off to essentially "pixelate" glare, which is a unique feature allowing for homogeneity to be manipulated in equivalent luminance conditions.

Figure 30:
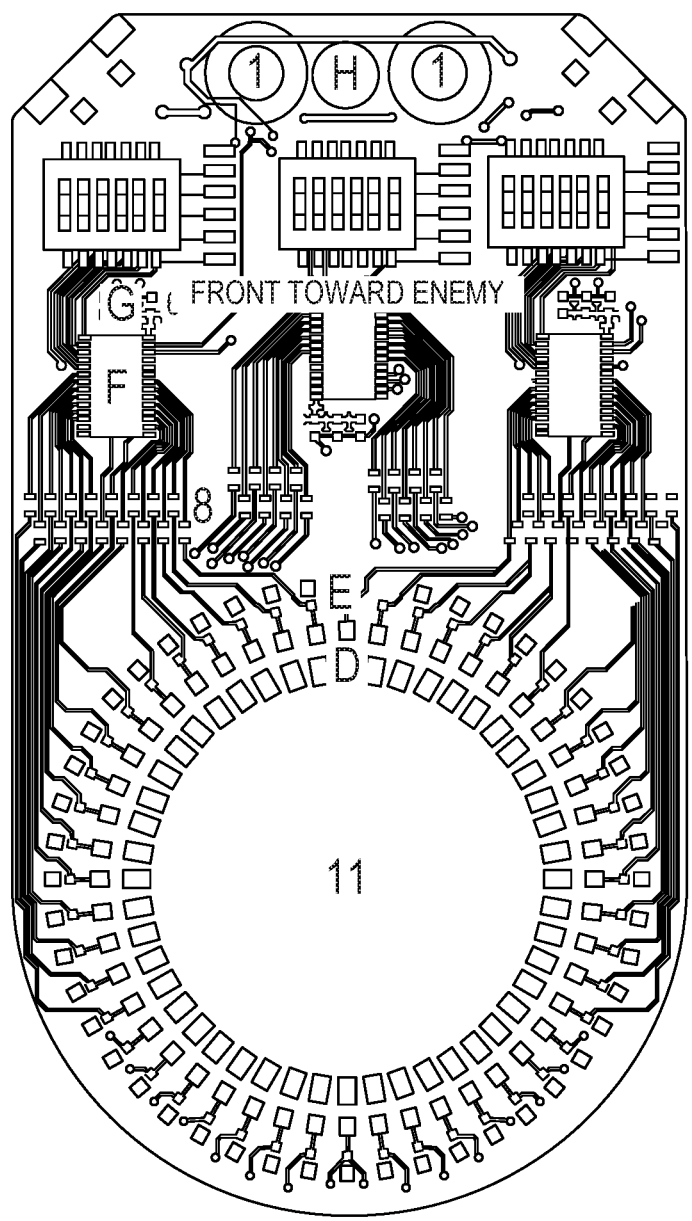
FIG. 30 is an alternative illustration showing the front side of a circuit board/device which generates the varying levels of light.
Figure 31:
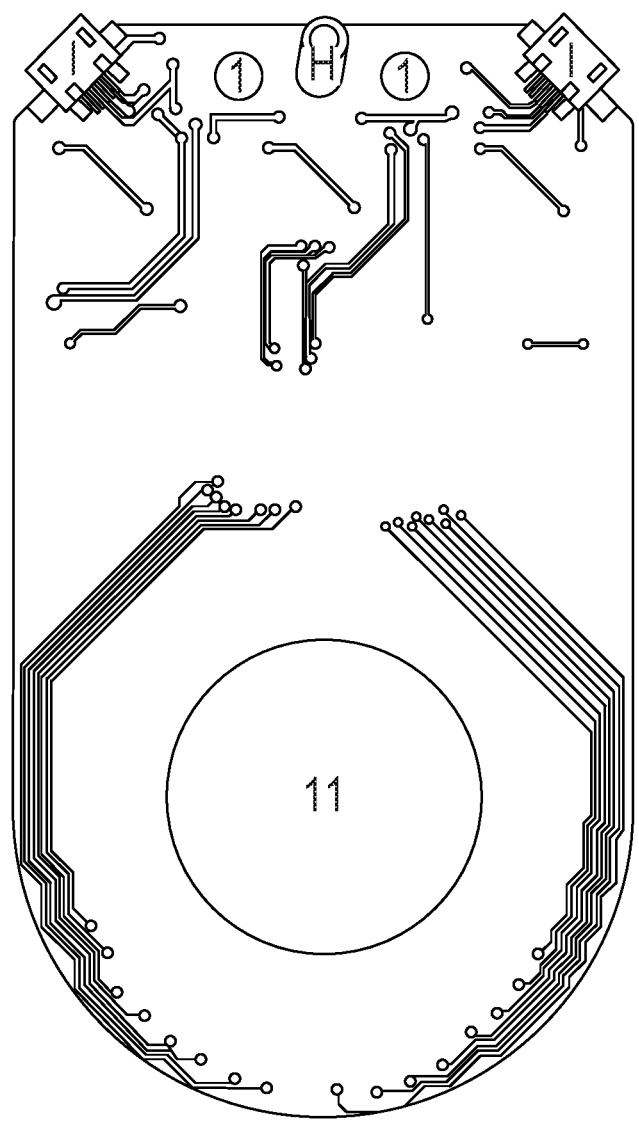
FIG. 31 is an alternative illustration showing the back side of a circuit board/device which generates the varying levels of light.

In an embodiment, the circuit board with the LEDs is controlled by a secondary board which connects to a computer via USB and custom software (FIG. 30).

In an embodiment, the device is also substantially smaller than other commercially available devices. In an embodiment, the LEDs, controller chips, resistors, I$^2$C/address resistors, thermal relief are on a single sided board. In an embodiment, the LEDs and controller chips are on the front of the board, while the I$^2$C/address resistors and thermal relief are on the back of the board. In an embodiment, the device can be a standalone device or mounted to a device/system which tests a test subject's vision. In an embodiment, the device can be connected to an integrated display. In an embodiment, the device can be mounted singularly (i.e., such as on an air rifle) or in a pair (i.e., for binocular vision testing). In an embodiment, the device can be worn on a test subject's face.

In an embodiment, the device can be mounted/positioned between the eye and scope of a rifle, or at the end of the scope to simulate different glare conditions in shooting, or behind a rear iron-sight of an air rifle. A stage with 3-axes of adjustment would allow changes to glare source to match eye-to-source distance with multiple head sizes and cheek weld preferences. A further embodiment includes a glare ring positioning assist system to make sure the device is of adequate distance away from subject to perform optimally.

In an embodiment, the device can be used, with some minor adjustments, as other tools, such as a hand-held clinical tool, worn in a driving or flying simulator, or mounted to work with a standardized eye chart assessment. In an embodiment, the device having 2 linear arrays of LEDs, which takes into account all peripheral vision, could be useful for flight simulators. The radial adjustment feature may also make this a useful tool in quantifying quality of outcome for different corneal surgical procedures, as glare related issues are a commonly reported post-surgical complication. This device may also be capable of simulating the effect of glare when photographing scenes, removing the need for photo manipulations.

The invention also provides for a glare testing device that assesses visual performance and discomfort under varying levels of veiling glare under photopic (e.g. "daytime") and mesopic (e.g. "twilight") lighting conditions. In an embodiment, the glare testing device uses the electronic device/system discussed above to generate the varying levels of glaring light which interferes with vision (i.e., glare source) (FIG. 1, and FIGS. 17-23). In an embodiment, the device can assess, for example, the influence of glare on marksmanship performance as well as visual performance. In some embodiments, the glare testing device is suitable for a desktop. In other embodiments, the glare testing device may be portable.

The invention also provides for method of assessing the visual performance of a test subject. In the glare testing device, a subject looks through an annular glare source (created by a ring of LEDs on a circuit board with a round void in the center) into a box which holds a small LCD monitor approximately 1 meter from the eye. The glare source and the LCD are both mounted onto frames that serve as panels (front and rear, respectively) of the box and the rear frame also allows for the mounting of a microcomputer (FIGS. 17-23). This microcomputer runs custom software for this device and sends signals to the microcontroller on the glare source to create veiling glare.

In a preferred embodiment, the glare source has a hole approximately 10-20 mm, preferably 15 mm, in radius and viewed from 25-30 mm, preferably 27.5 mm. Hole size or plate position can be adjusted according to formula 1 (from Moreno, I., Avendaño-Alejo, M., & Tzonchev, R. I. (2006). Designing light-emitting diode arrays for uniform near-field irradiance. Applied optics, 45(10), 2265-2272):

$$\text{Hole radius} = \tan(28.6 \text{ degrees}) \times (27.5 \text{ mm} + \text{board-to-plate distance}) \quad \text{Formula 1}$$

The formula depends on the LED reflector geometry in addition to the arrangement of the LEDs.

Figure 4A:
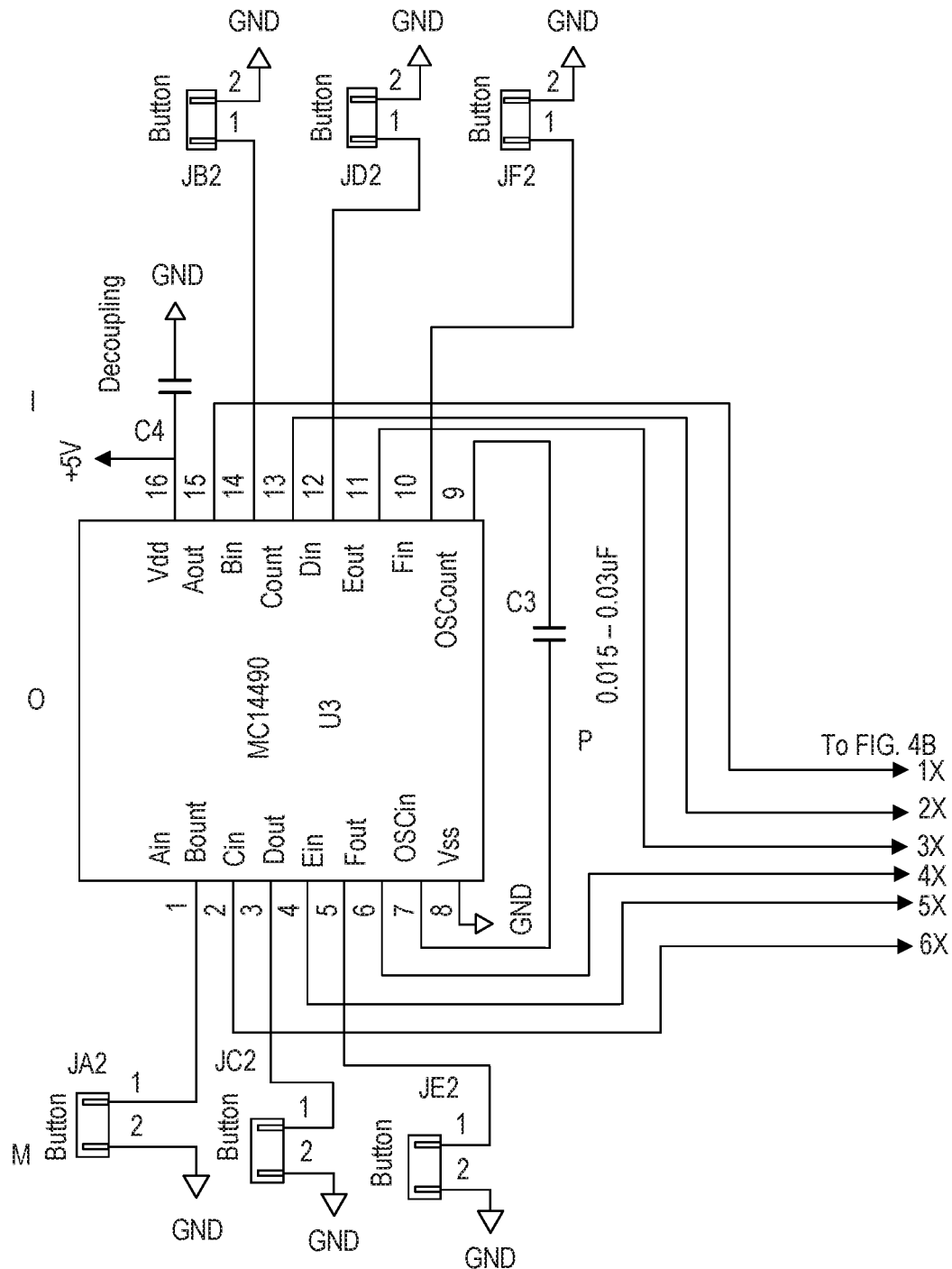
FIGS. 4(A) and (B) are schematics illustrating assessments of decoupling capacitors for a glare source and wiring of a hex-inverter used in an input device for certain embodiments.
Figure 4B:
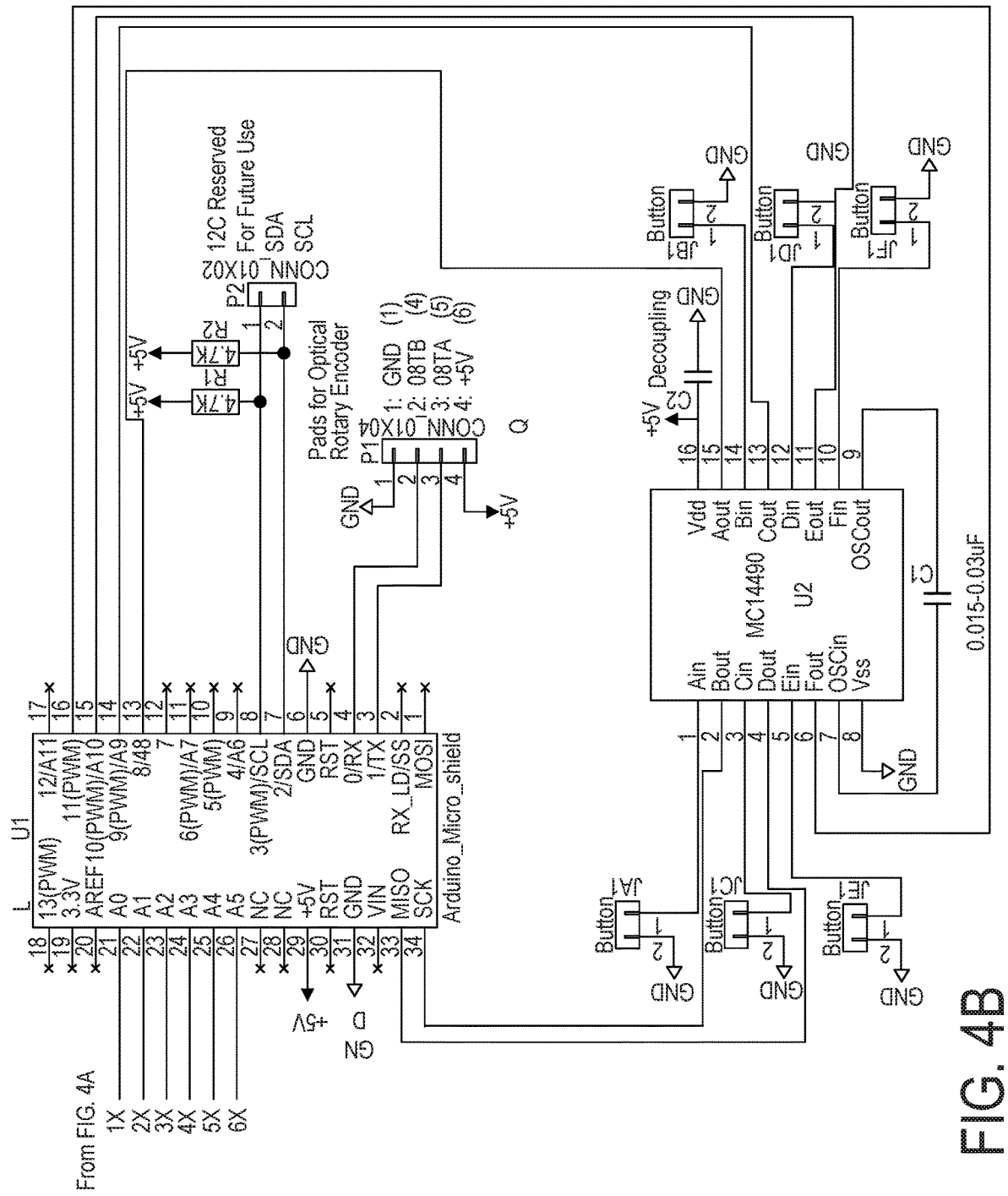
Figure 5:
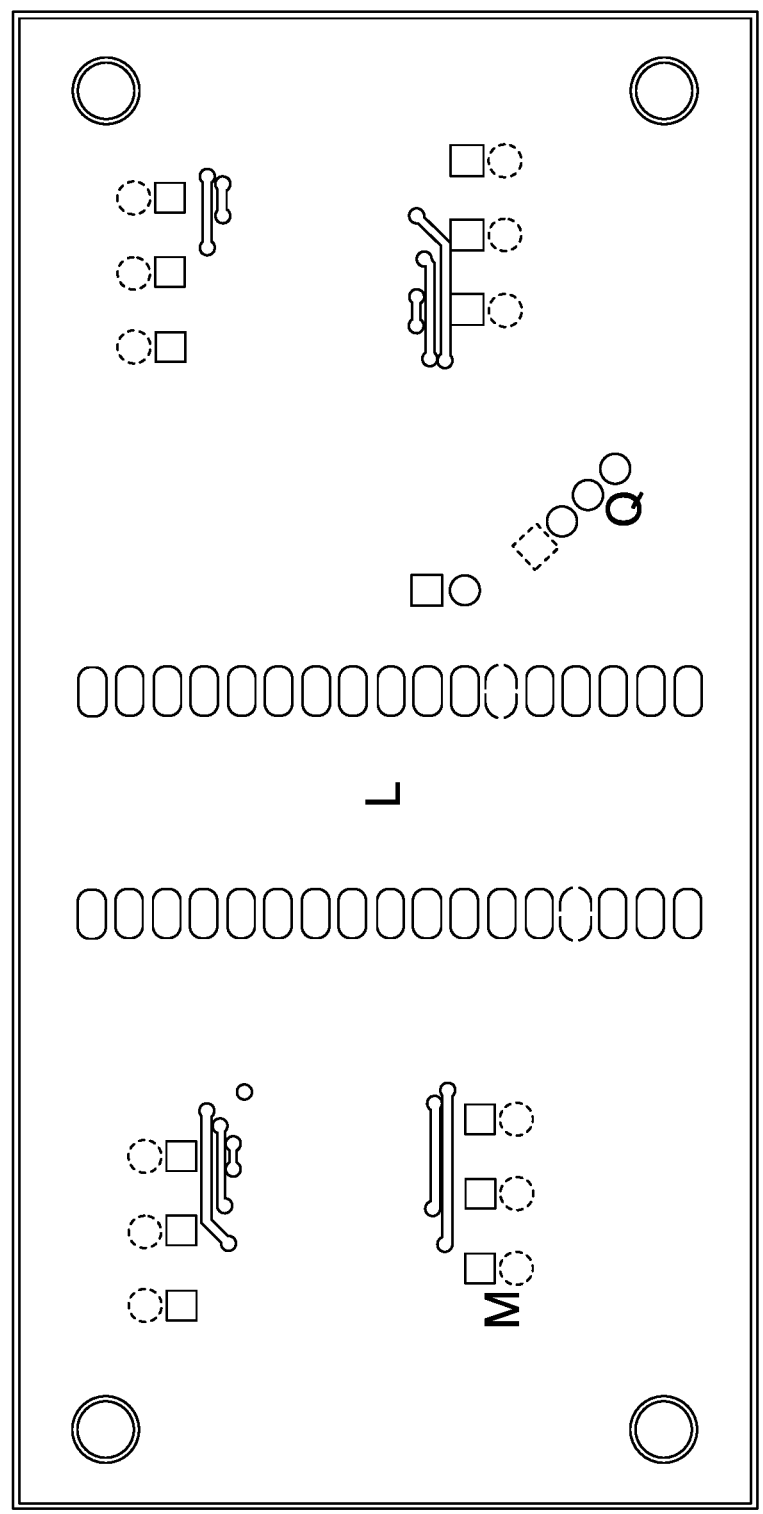
FIG. 5 illustrates conception of test setting selections in a user-interface compatible with input hardware manageable under low-illumination levels in certain embodiments.
Figure 6:
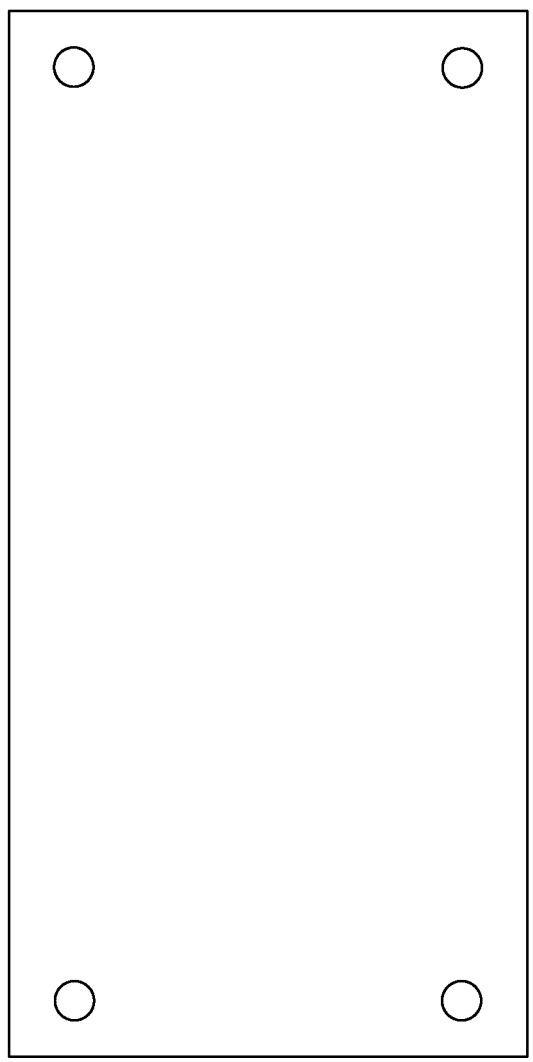
FIG. 6 is a schematic illustrating a layout of a printed circuit board of a desktop input device in certain embodiments.
Figure 7:
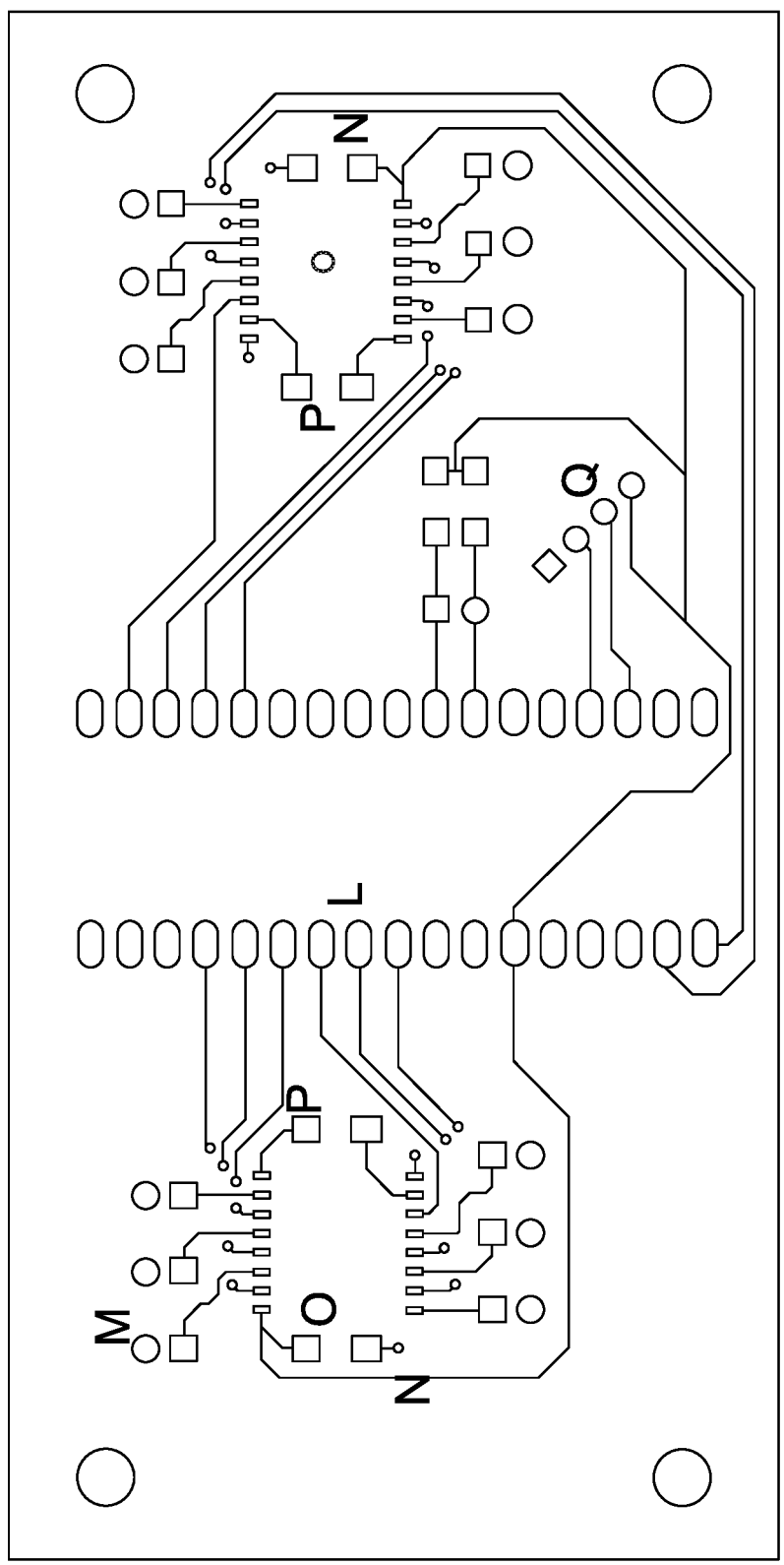
FIG. 7 is a schematic illustrating a bottom copper layer of a printed circuit board for a desktop input device in certain embodiments.
Figure 8:
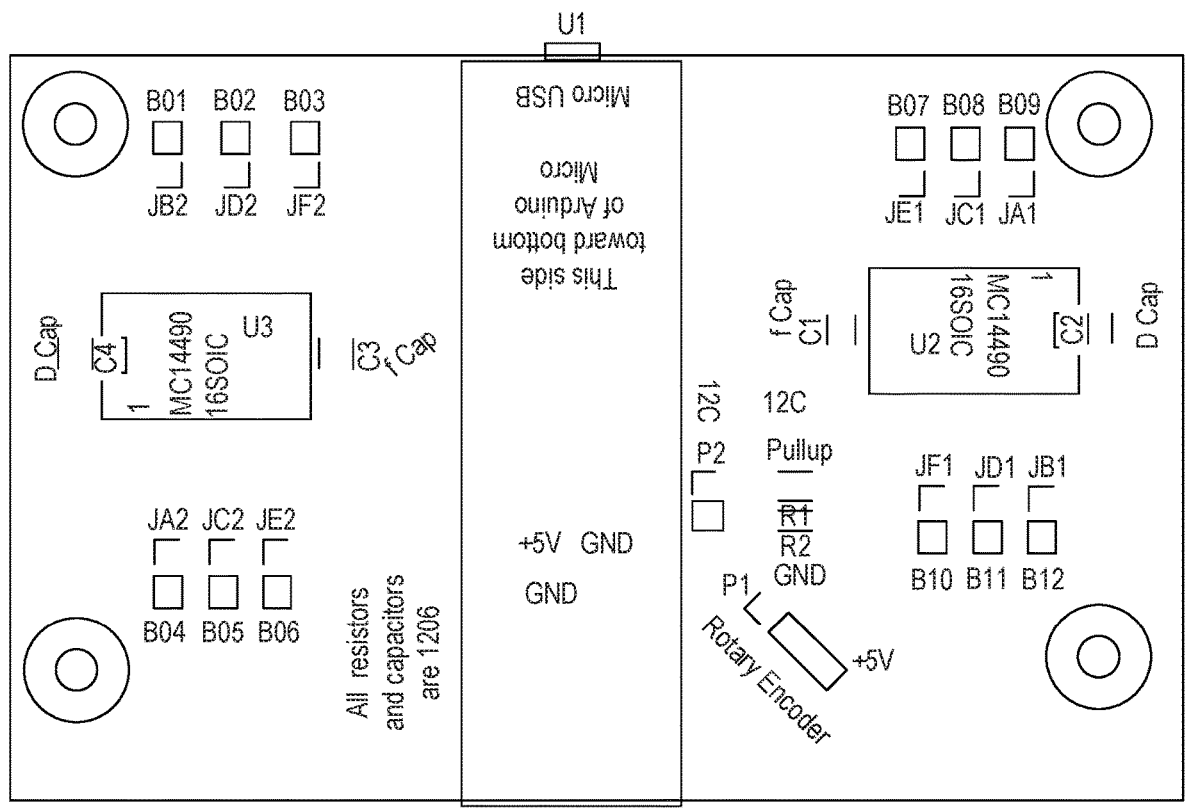
FIG. 8 is a schematic illustrating a bottom silk screen layer of a printed circuit board for an desktop input device in certain embodiments.
Figure 9A:
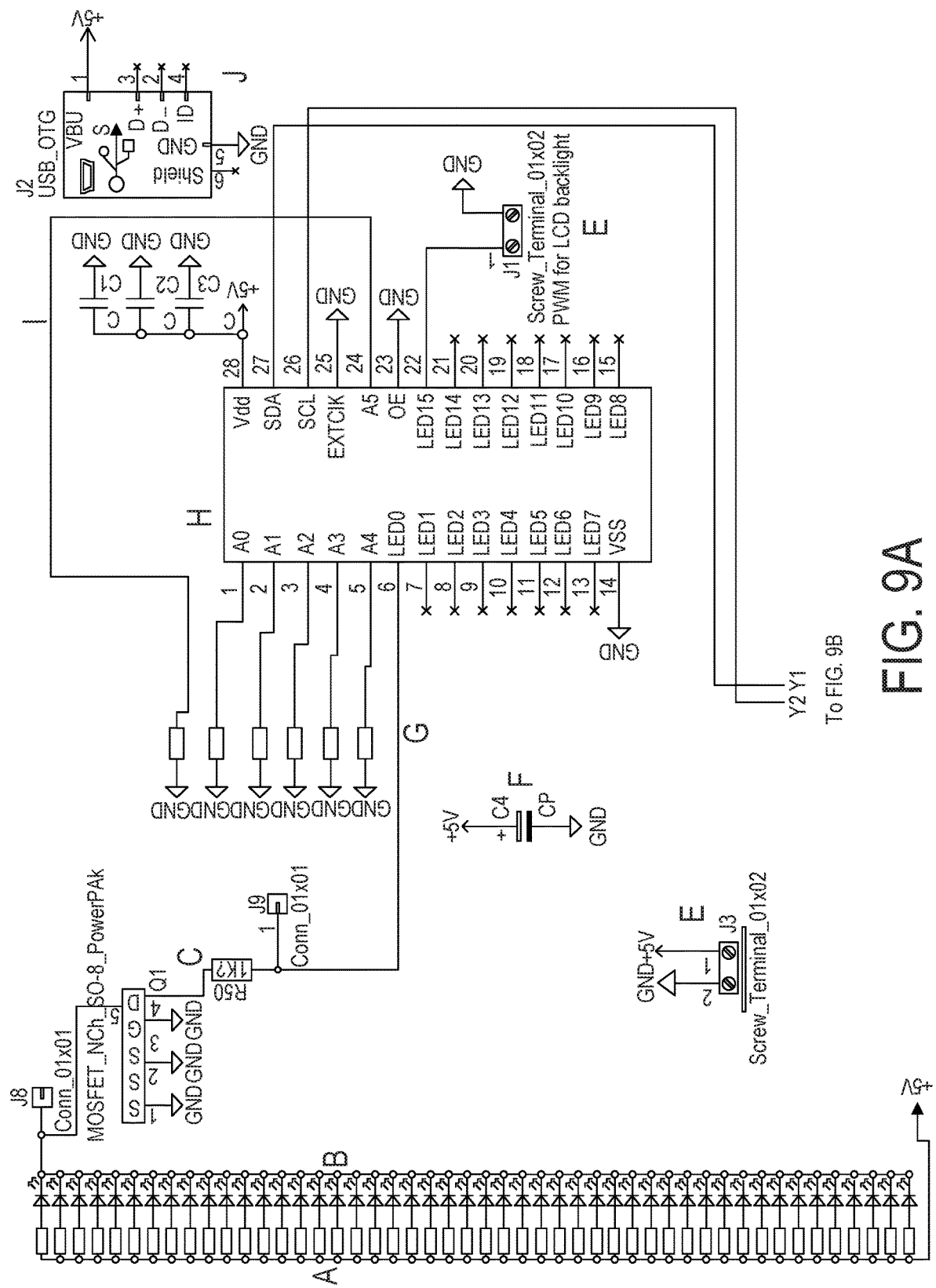
FIGS. 9(A) and (B) are schematics illustrating a top copper layer of a printed circuit board for a desktop input device in certain embodiments.
Figure 9B:
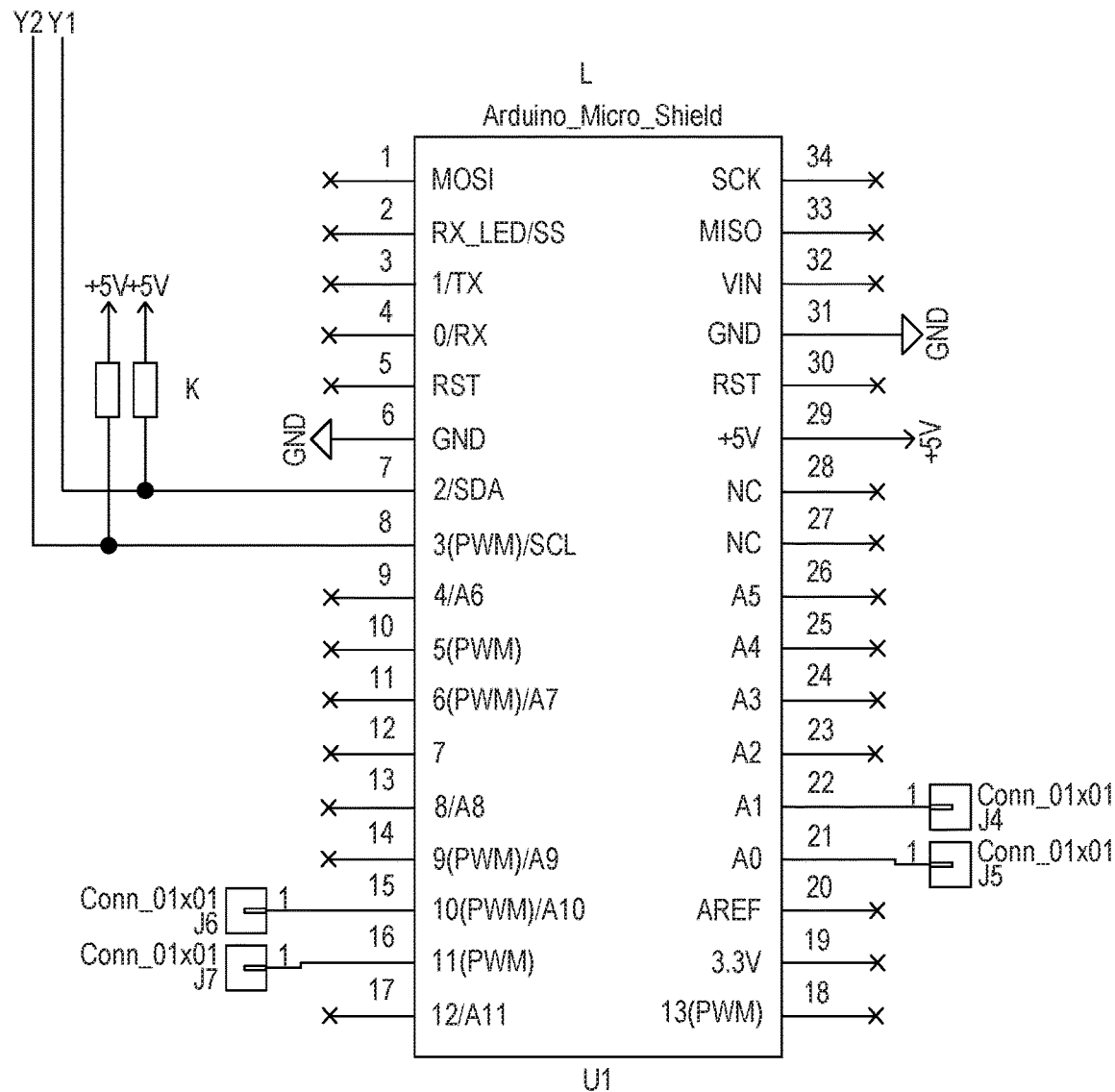
Figure 10:
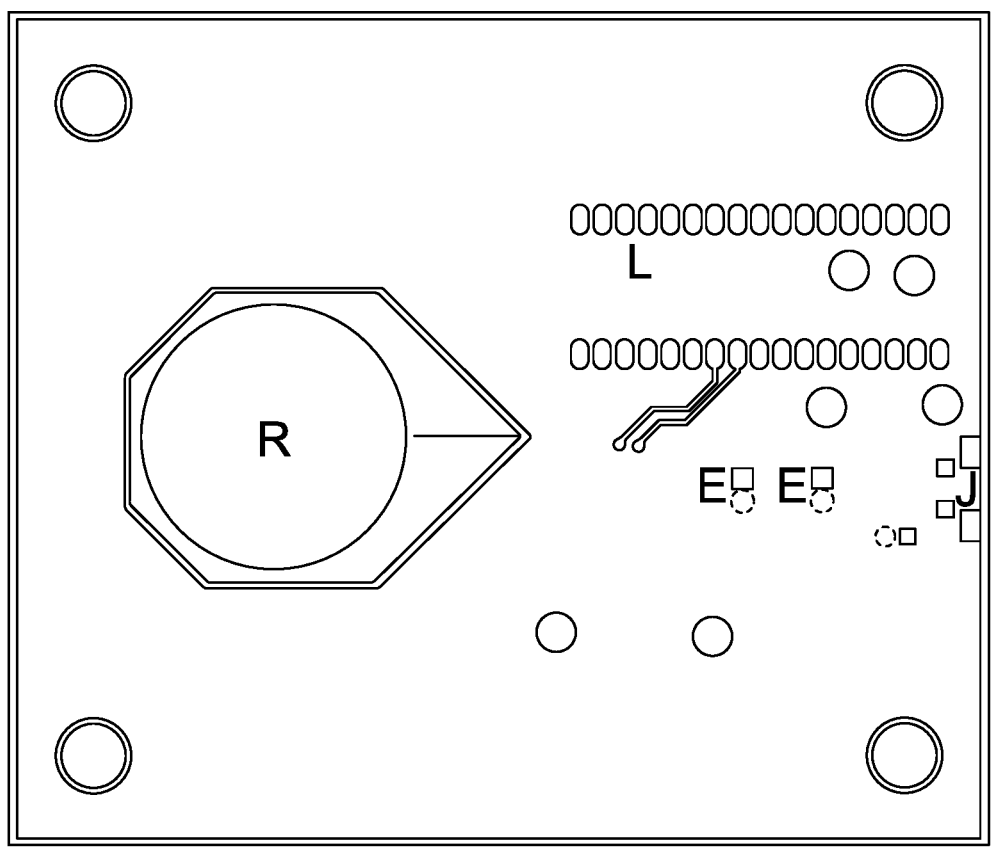
FIG. 10 is a schematic illustrating a top silkscreen layer of a printed circuit board files for a desktop input device in certain embodiments.
Figure 11:
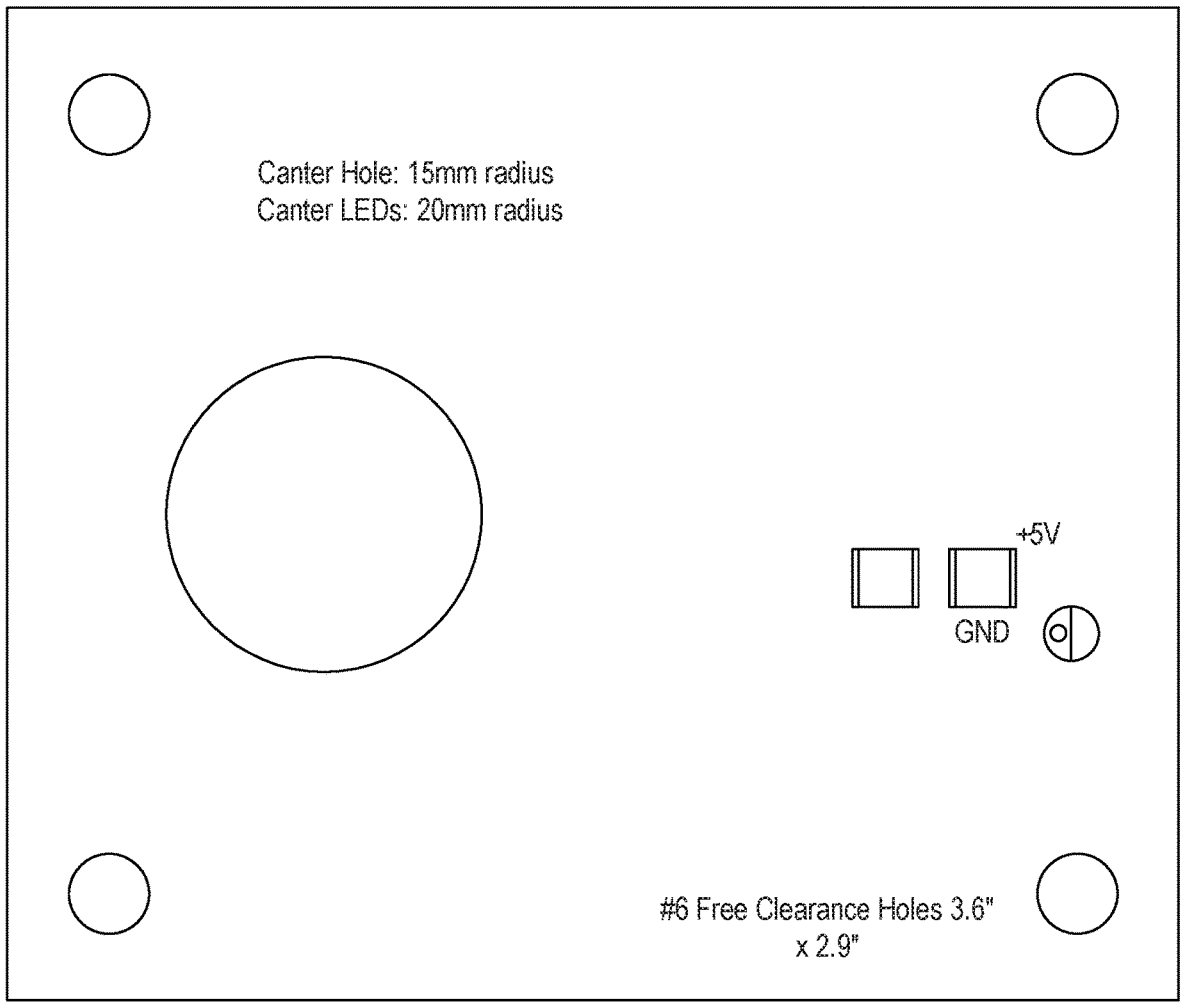
FIG. 11 is a schematic illustrating a layout used to generate printed circuit board files for a desktop glare source in certain embodiments.
Figure 12:
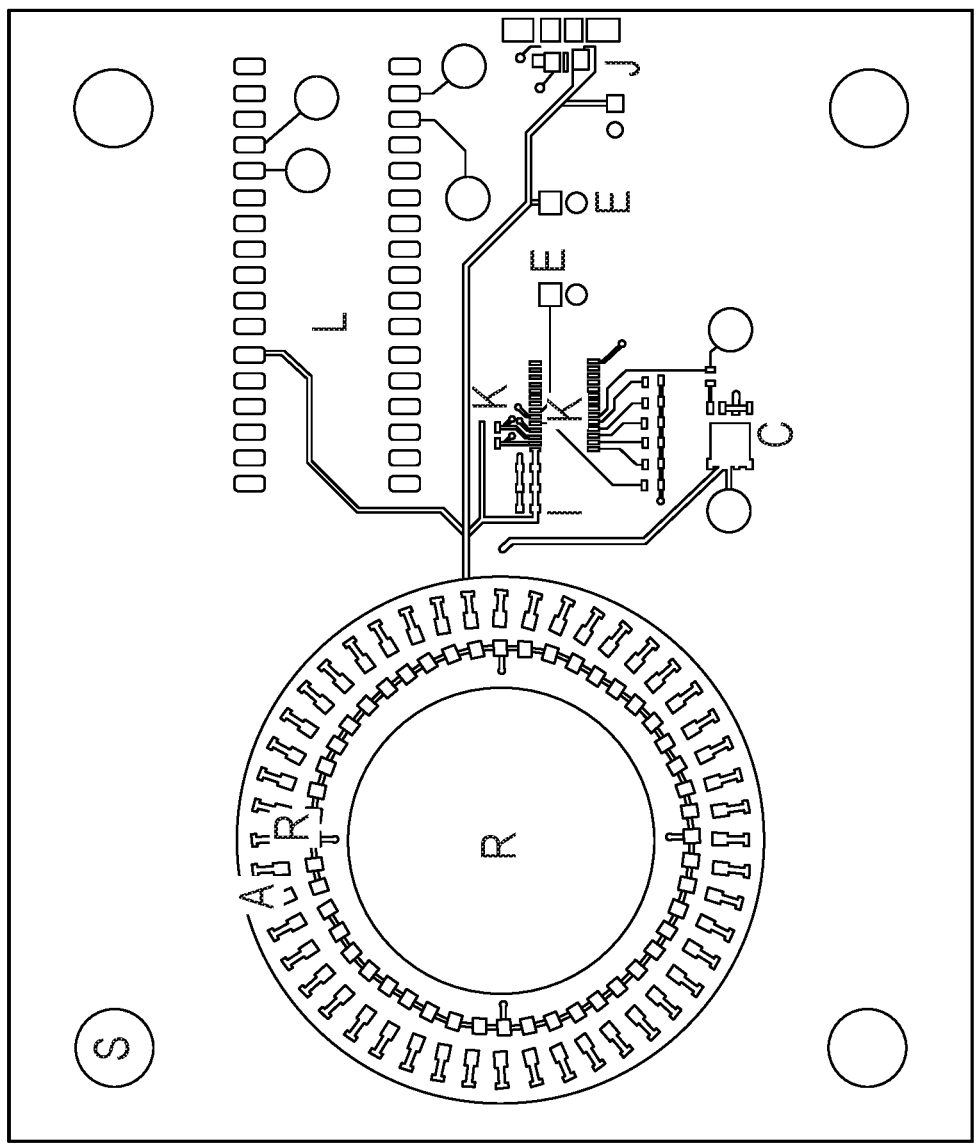
FIG. 12 is a schematic illustrating a bottom copper layer of a printed circuit board for a desktop glare source in certain embodiments.
Figure 13:
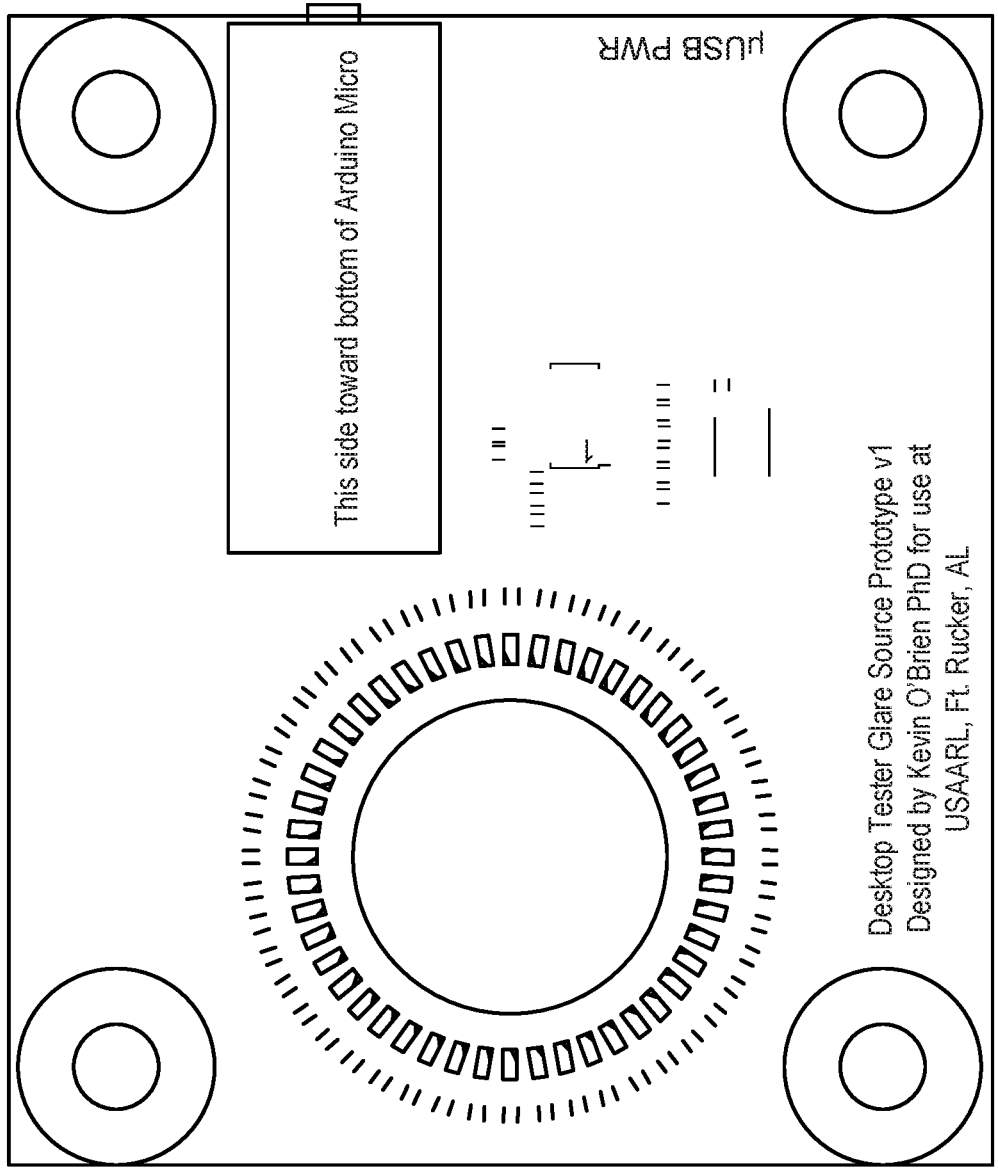
FIG. 13 is a schematic illustrating a bottom silk screen layer of a printed circuit board for a desktop glare source in certain embodiments.
Figure 14:
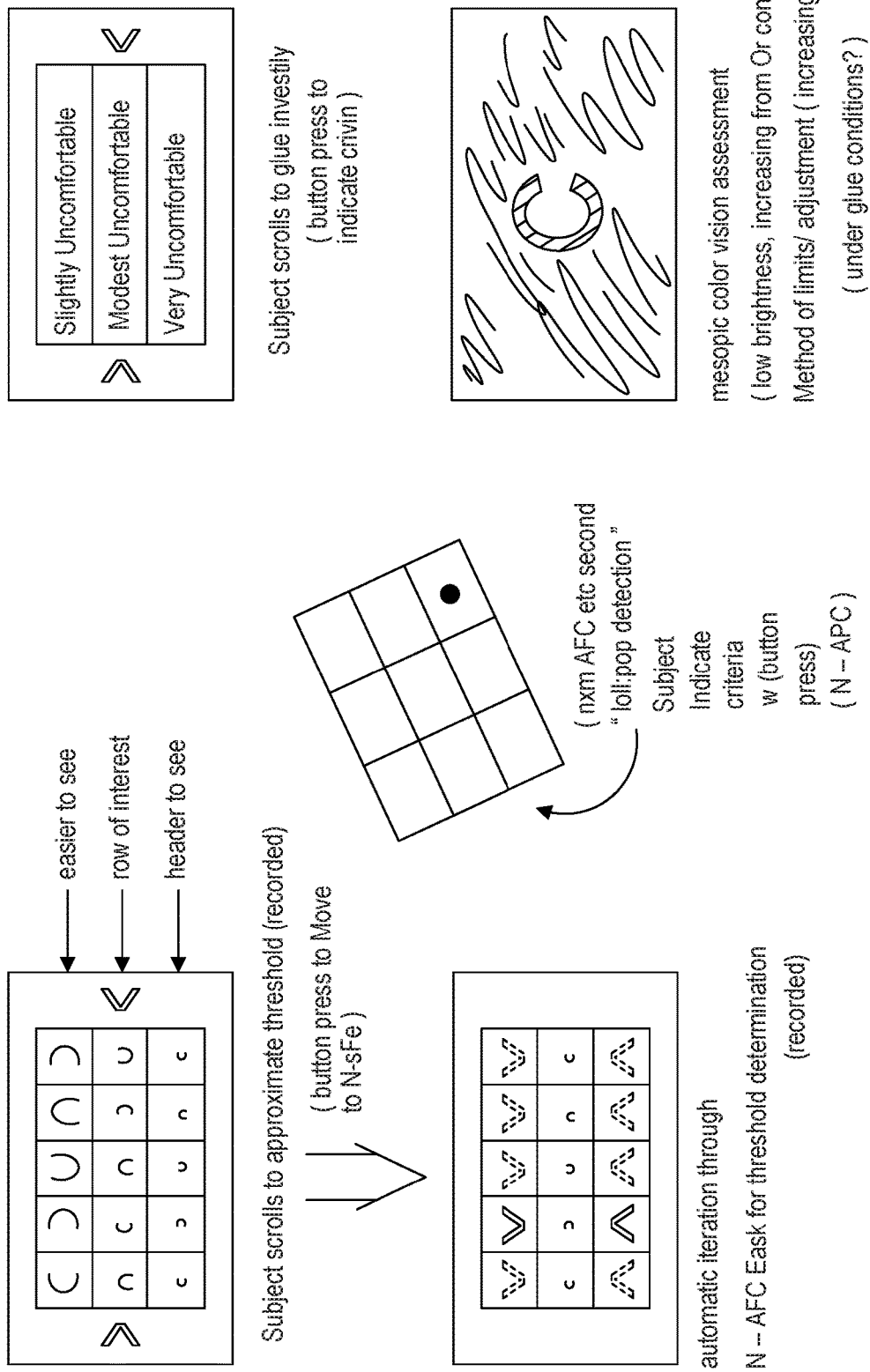
FIG. 14 is a schematic illustrating a front copper layer of a printed circuit board for a desktop glare source in certain embodiments.
Figure 15A:
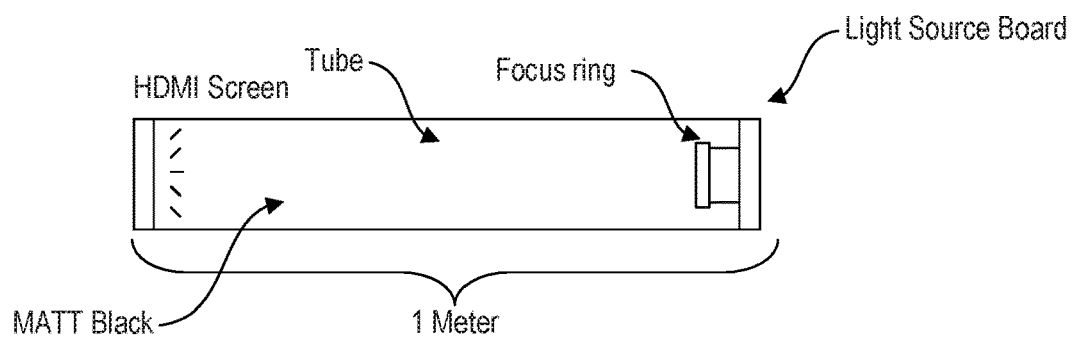
FIGS. 15(A) and (B) are schematics illustrating a front silkscreen layer of a printed circuit board for a desktop glare source in certain embodiments. (A) Top section contains drawings for the enclosure to which the glare source and target display are mounted. Bottom section is a diagram of the shape needed for a 3D-printed component which would protect the circuit board of the glare source from contact with research subjects. (B) shows the glare-source circuit board with dimensional measurements.
Figure 15B:
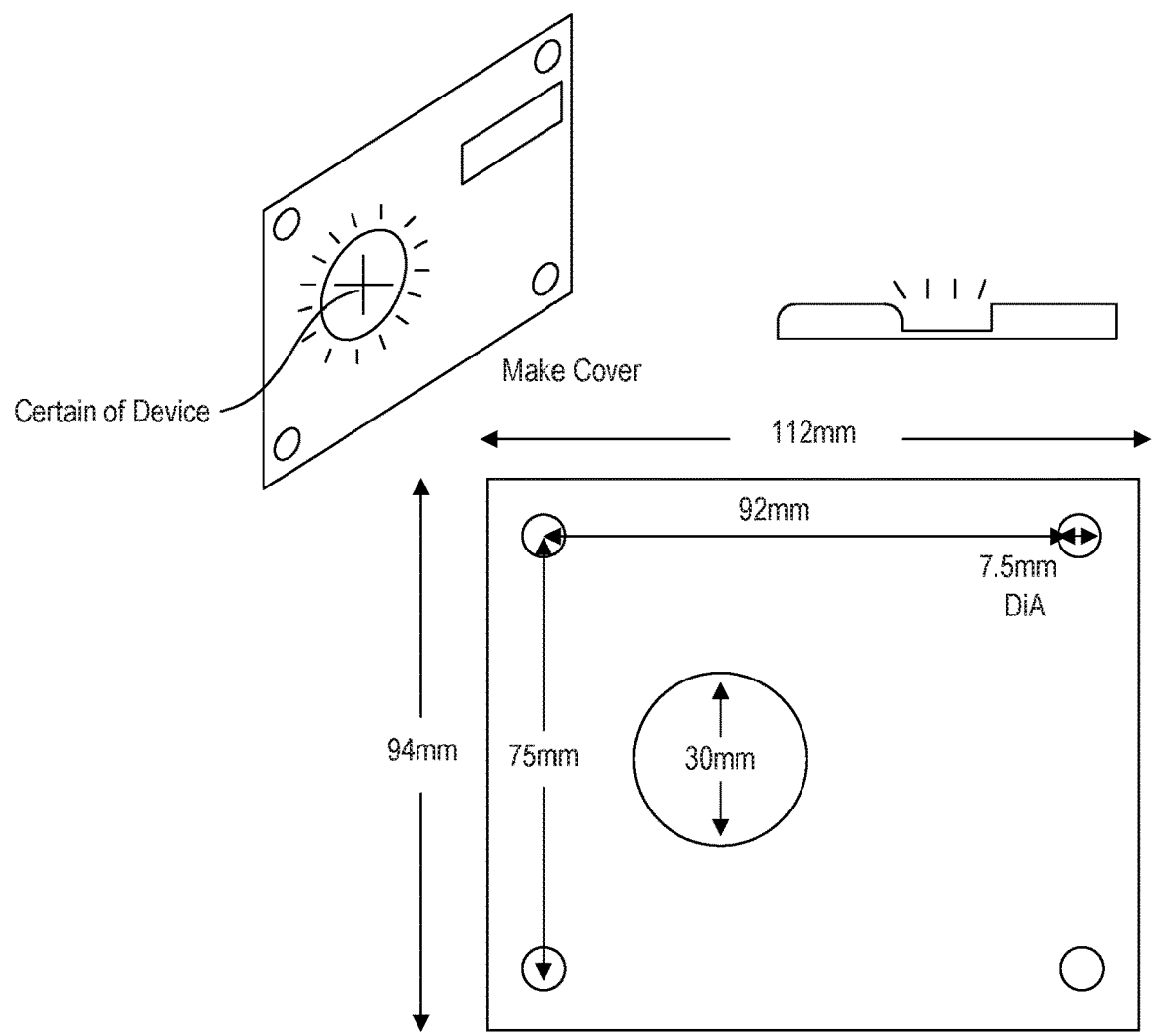
Figure 16:
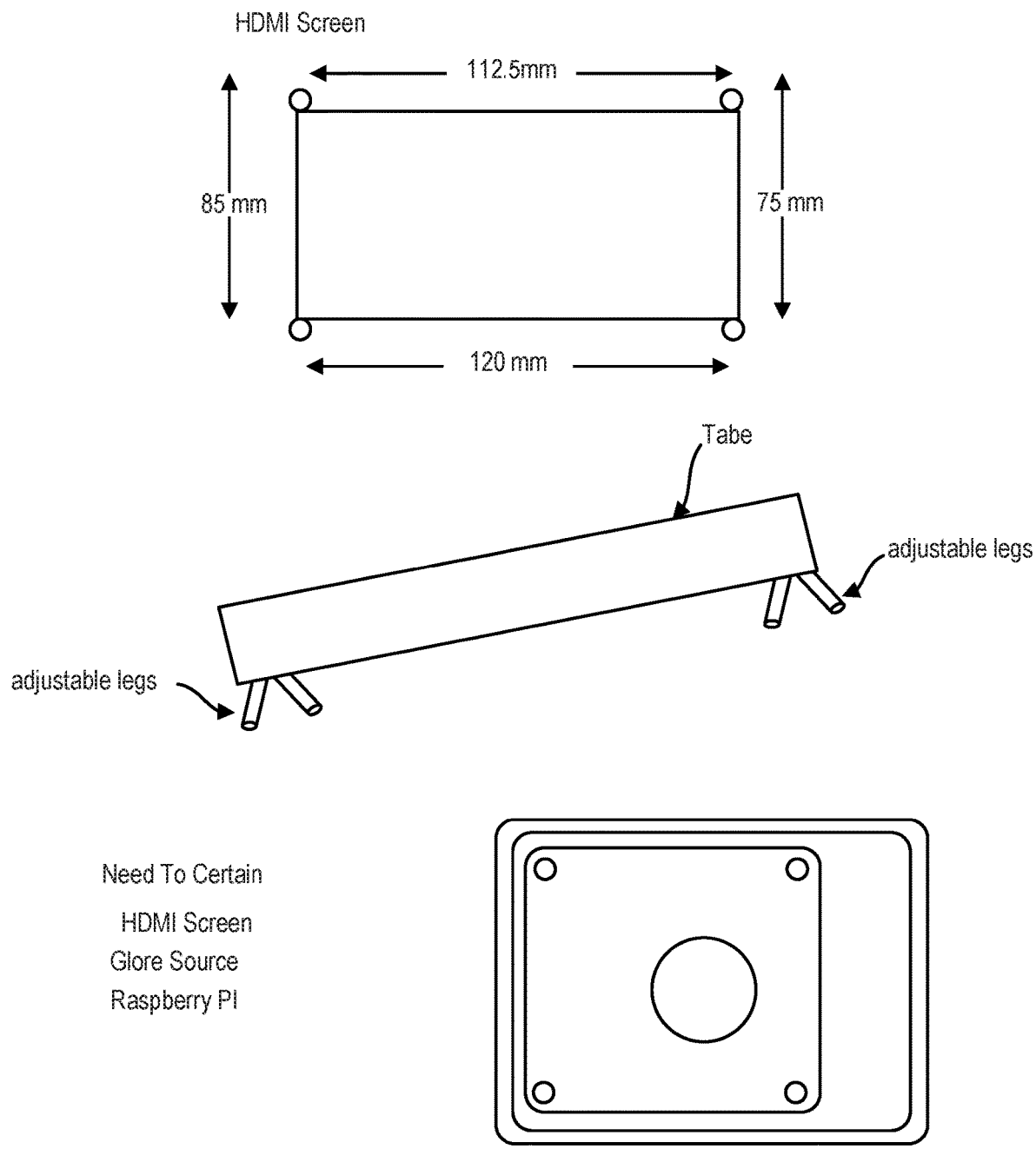
FIG. 16 is an illustration of layouts of intended assessments in certain embodiments.
Figure 17:
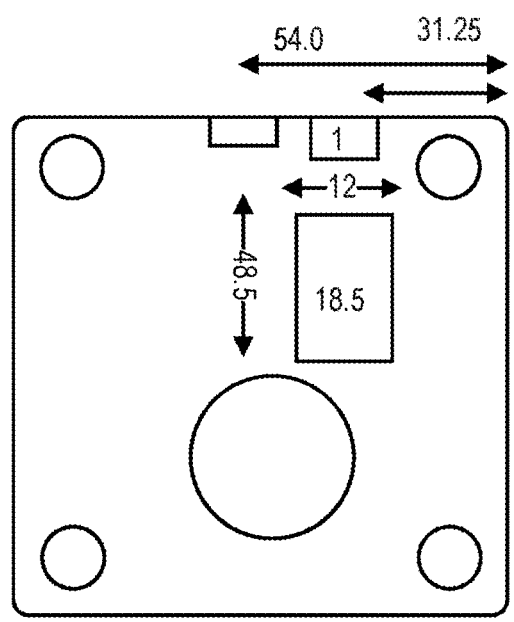
FIG. 17 is a representation of a glare source in certain embodiments.
Figure 18:
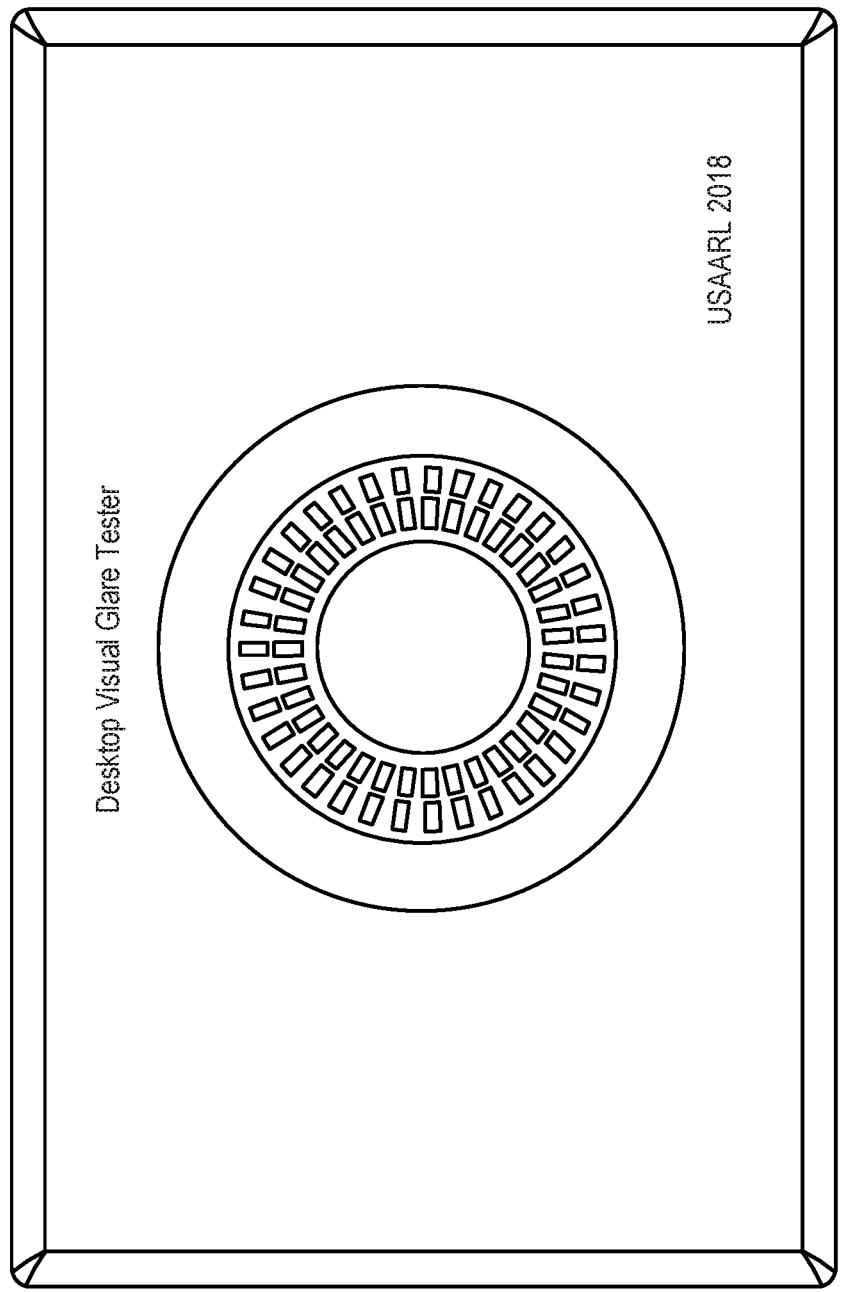
FIG. 18 is an illustration depicting a front plate of an enclosure with an exposed portion of a desktop visual glare tester in certain embodiments.
Figure 19:
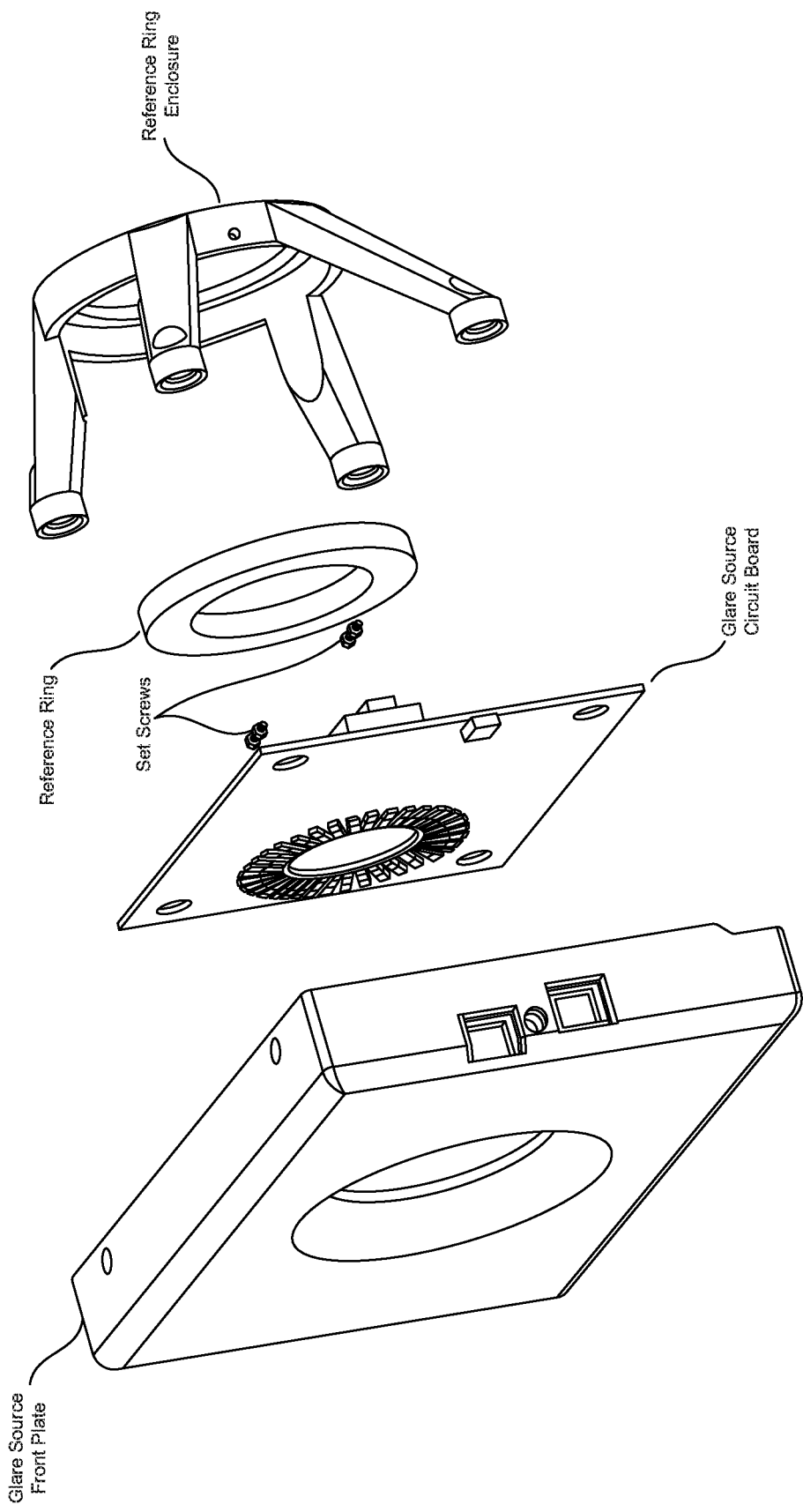
FIG. 19 is an illustration depicting a front plate of a glare source, a reference ring, and a reference ring enclosure of a desktop visual glare tester in certain embodiments.
Figure 20:
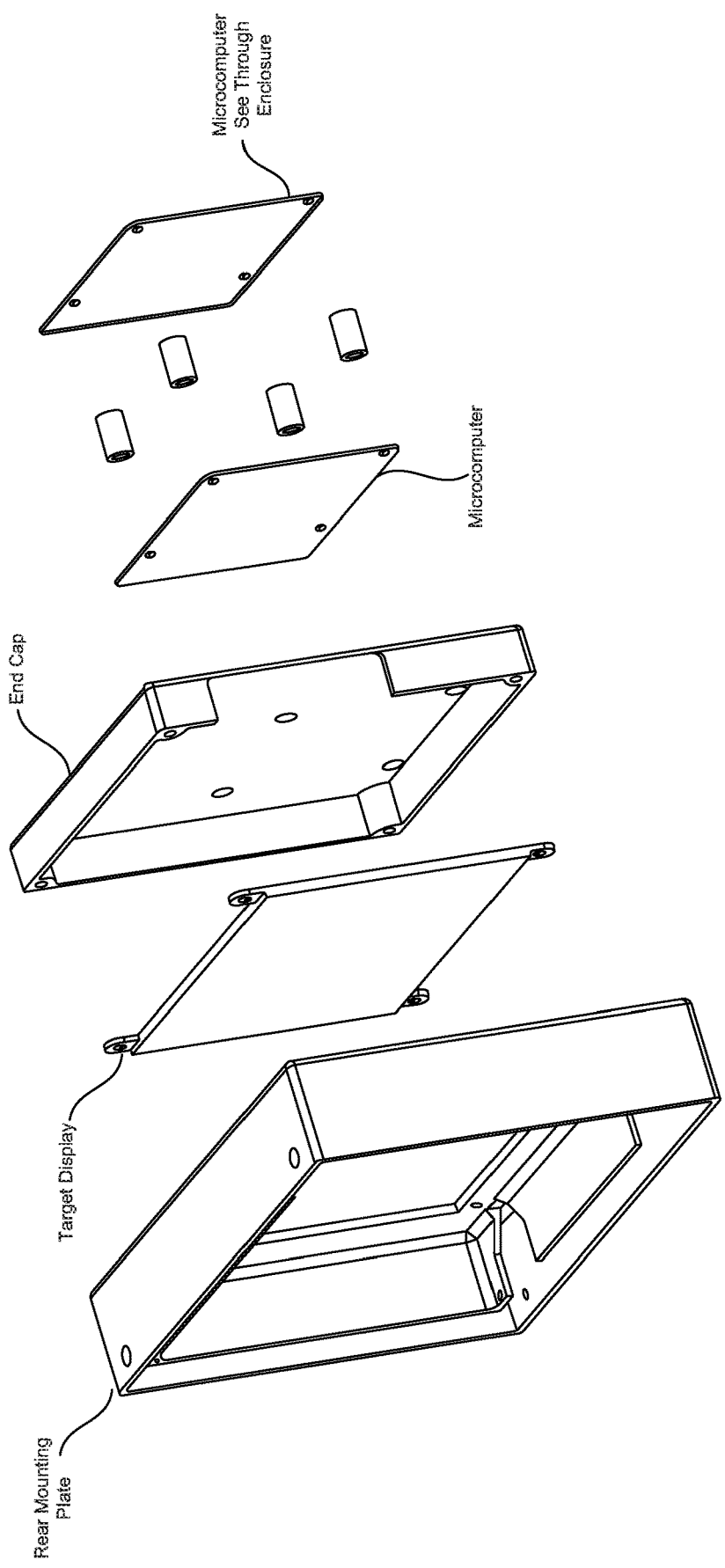
FIG. 20 is an illustration depicting a rear mounting plate, a target display, an end cap, and a microcomputer enclosure for a desktop visual glare tester in certain embodiments.
Figure 21:
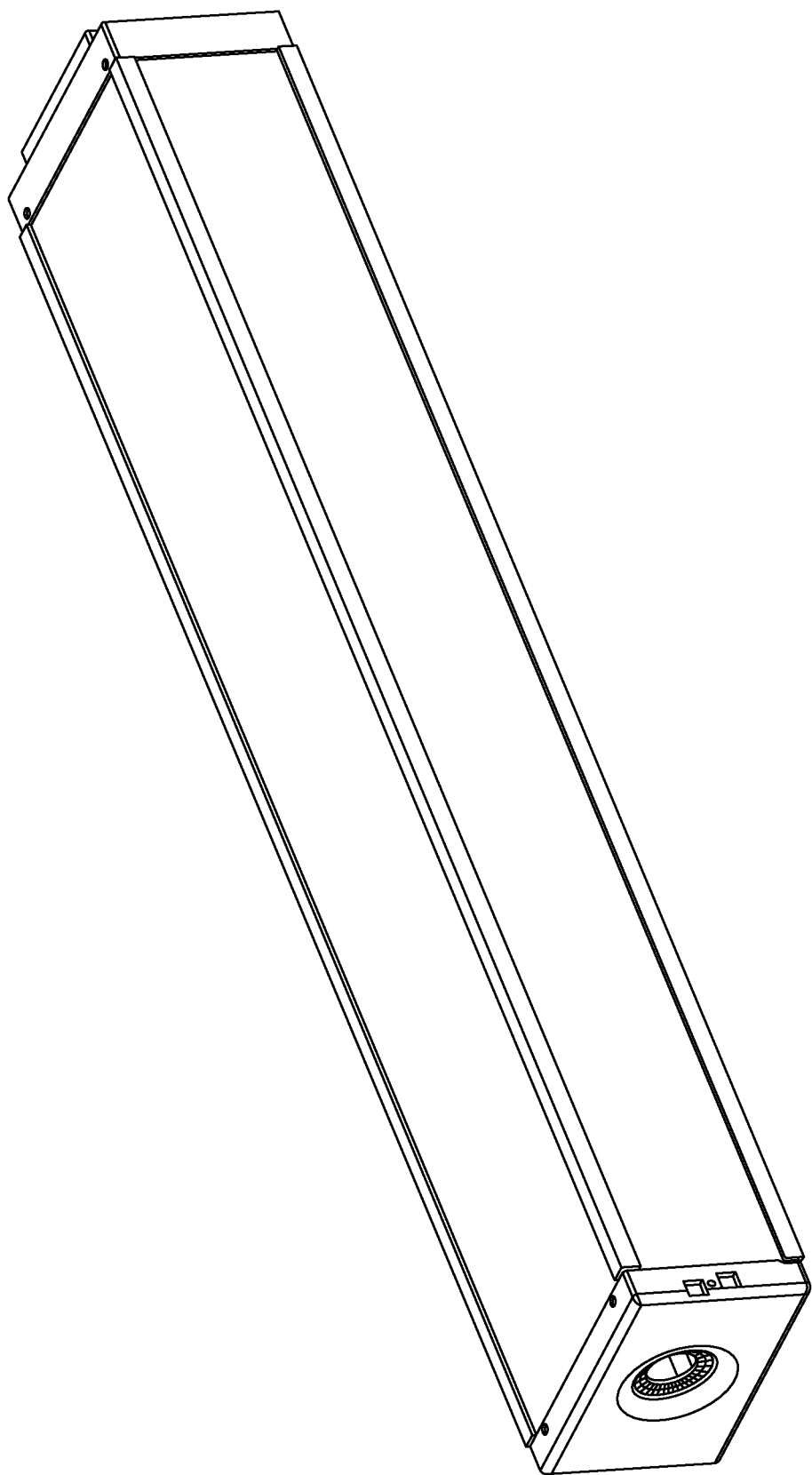
FIG. 21 is an illustration depicting a front plate and a rear plate installed on a main enclosure body for a desktop visual glare tester in certain embodiments.
Figure 22:
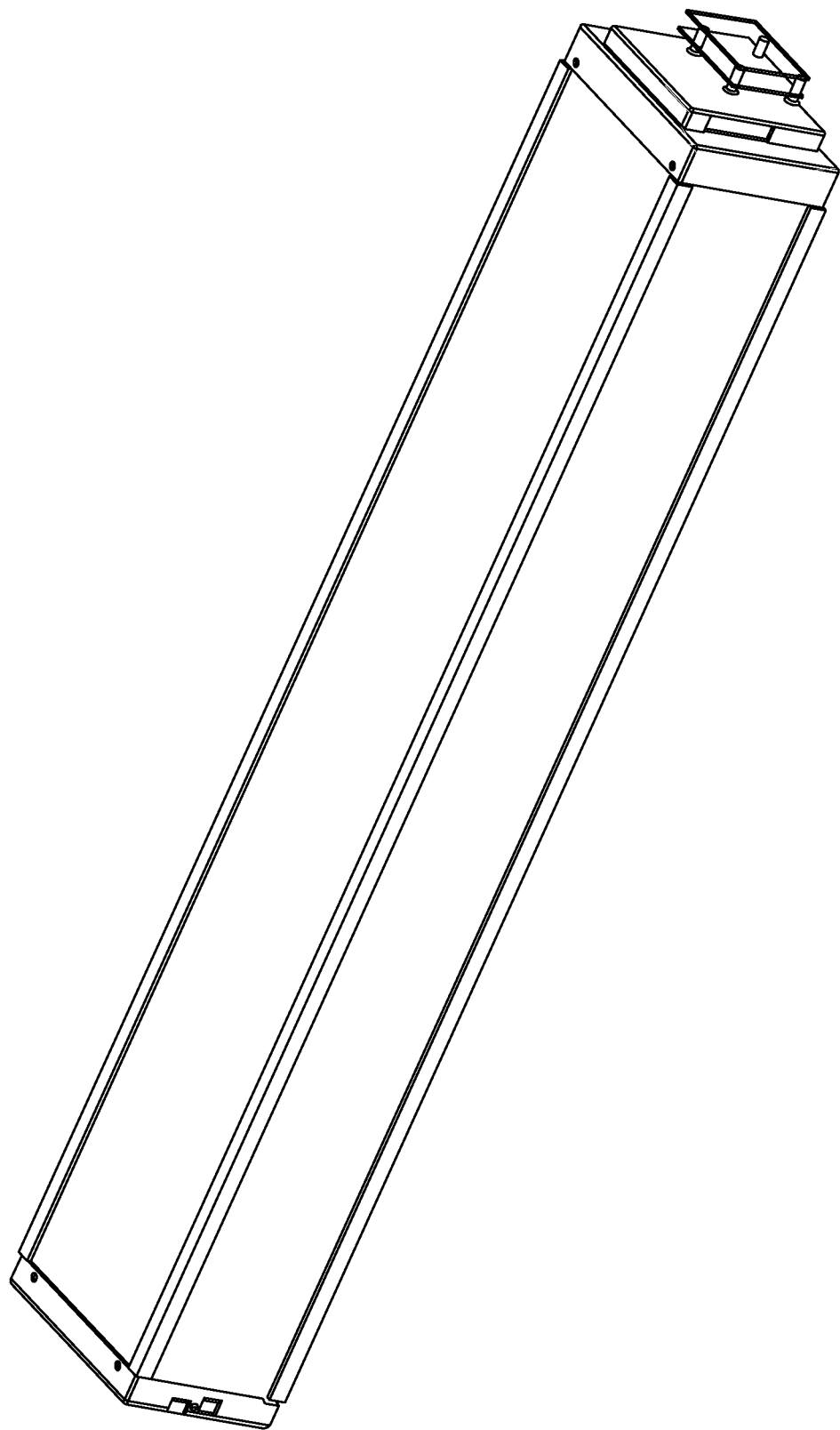
FIG. 22 is an illustration depicting a front plate and a rear plate installed on a main enclosure body for a desktop visual glare tester in certain embodiments.
Figure 23:
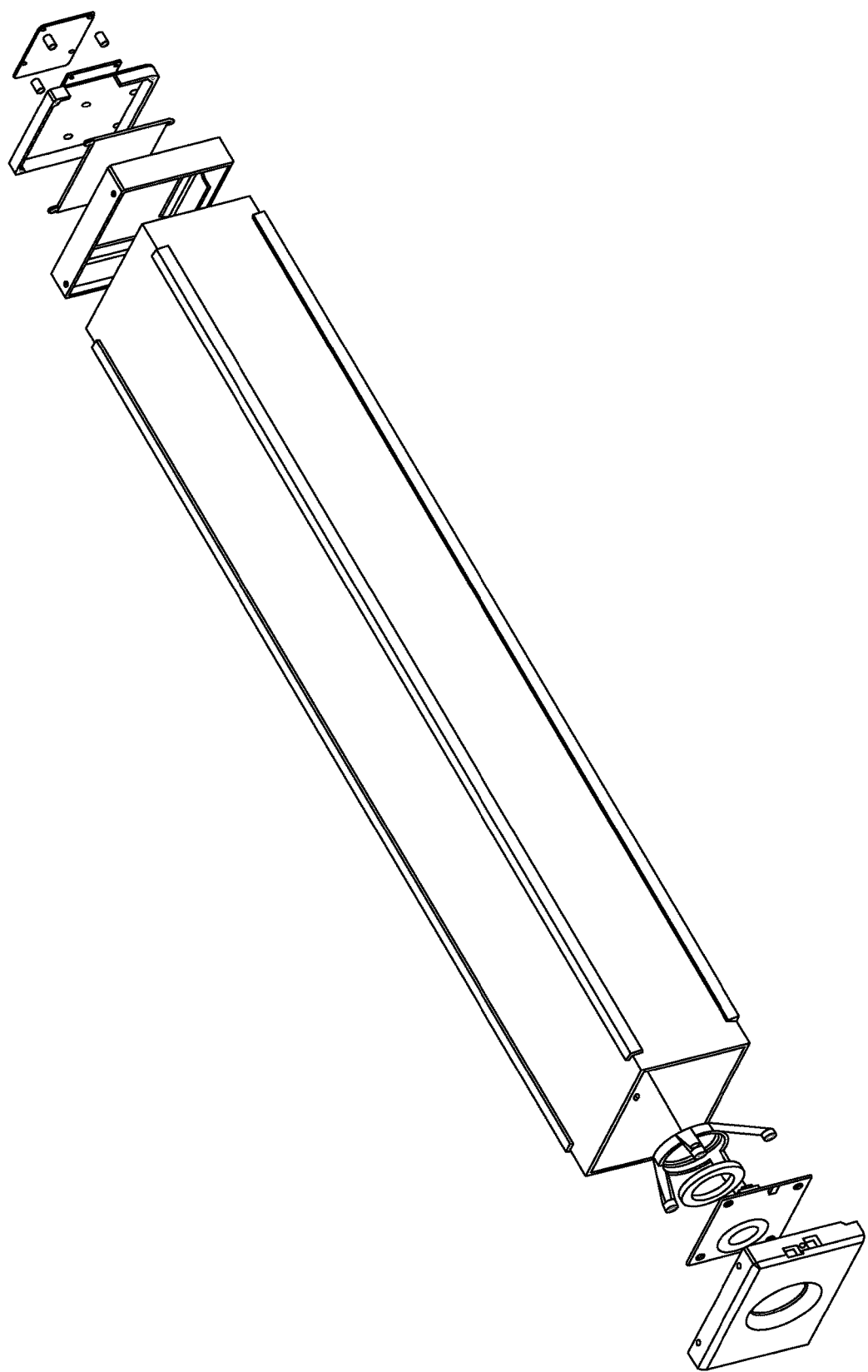
FIG. 23 is an illustration depicting an exploded view of enclosure components for a desktop visual glare tester in certain embodiments.
Figure 24A:
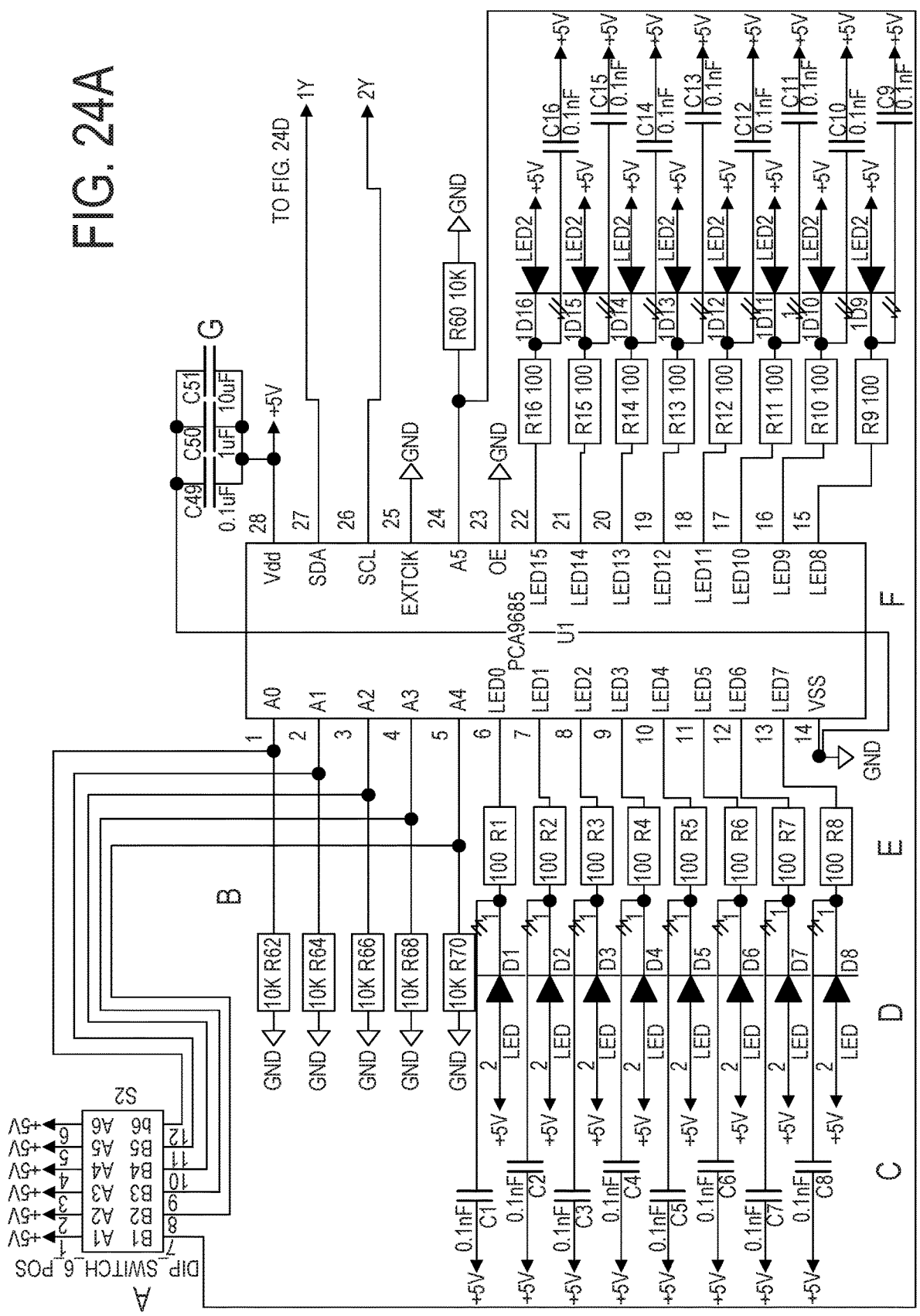
FIG. 24(A)-(D) are schematic diagrams of the circuit wherein the LEDs are independently controlled.
Figure 24B:
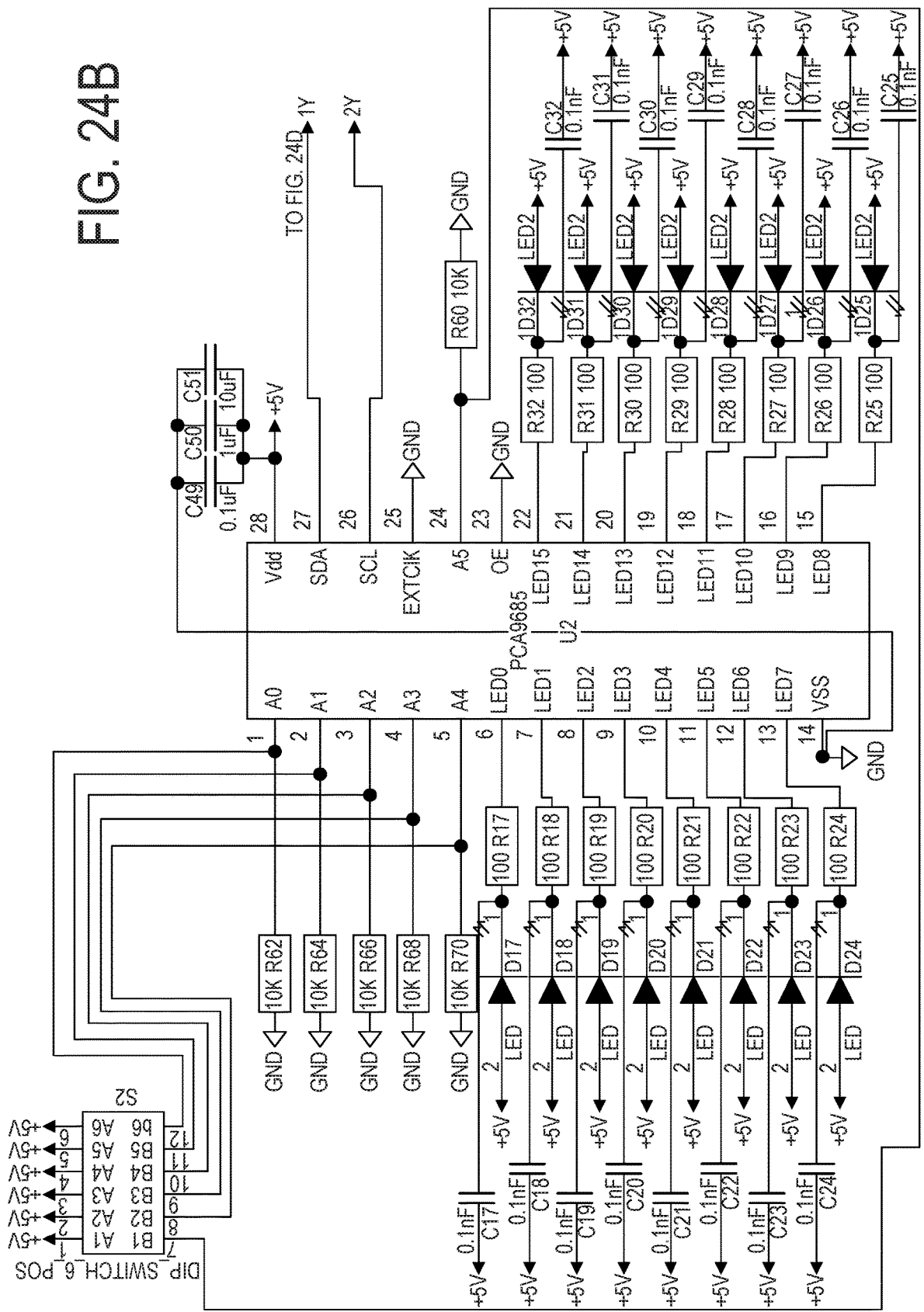
Figure 24C:
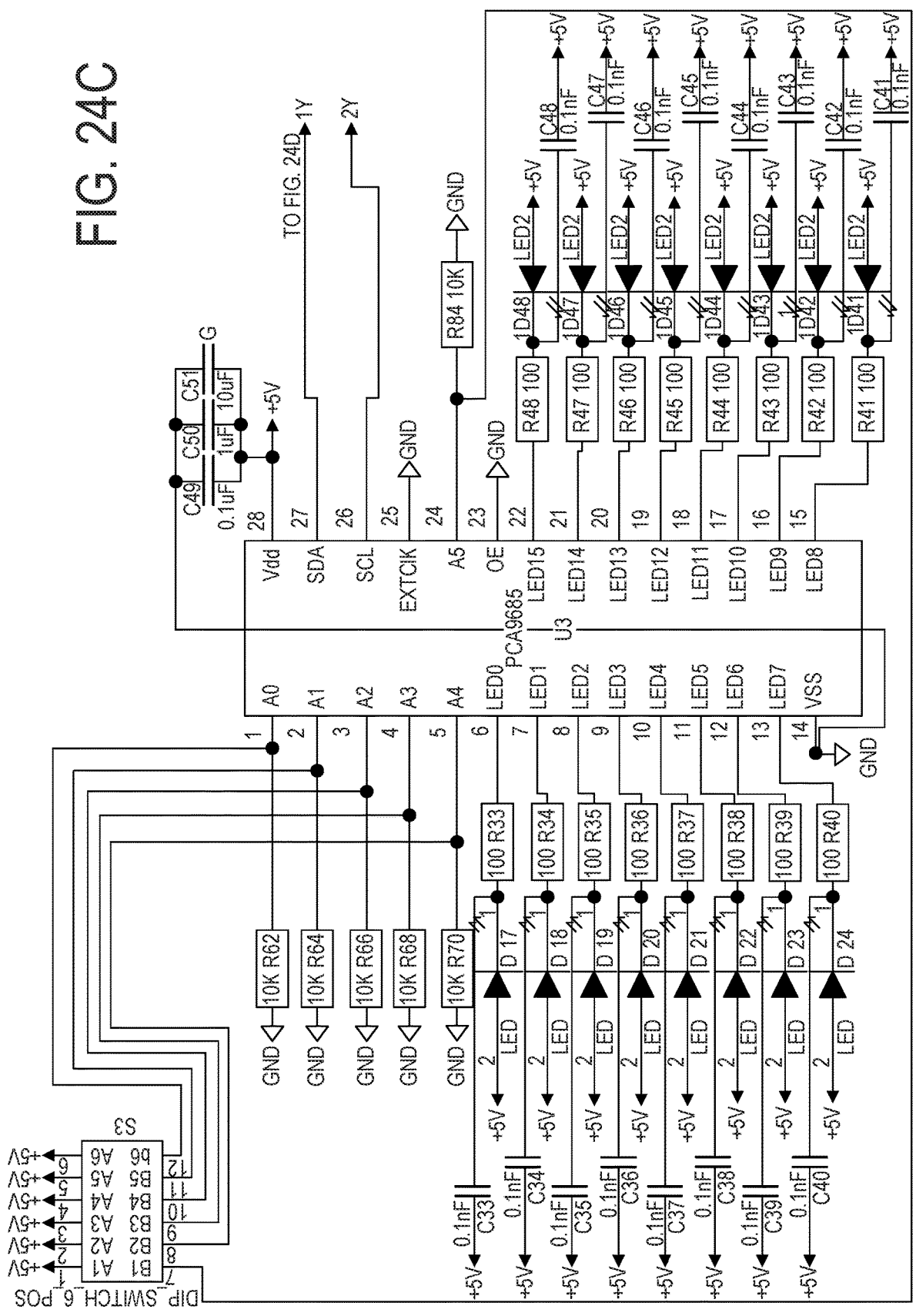
Figure 24D:
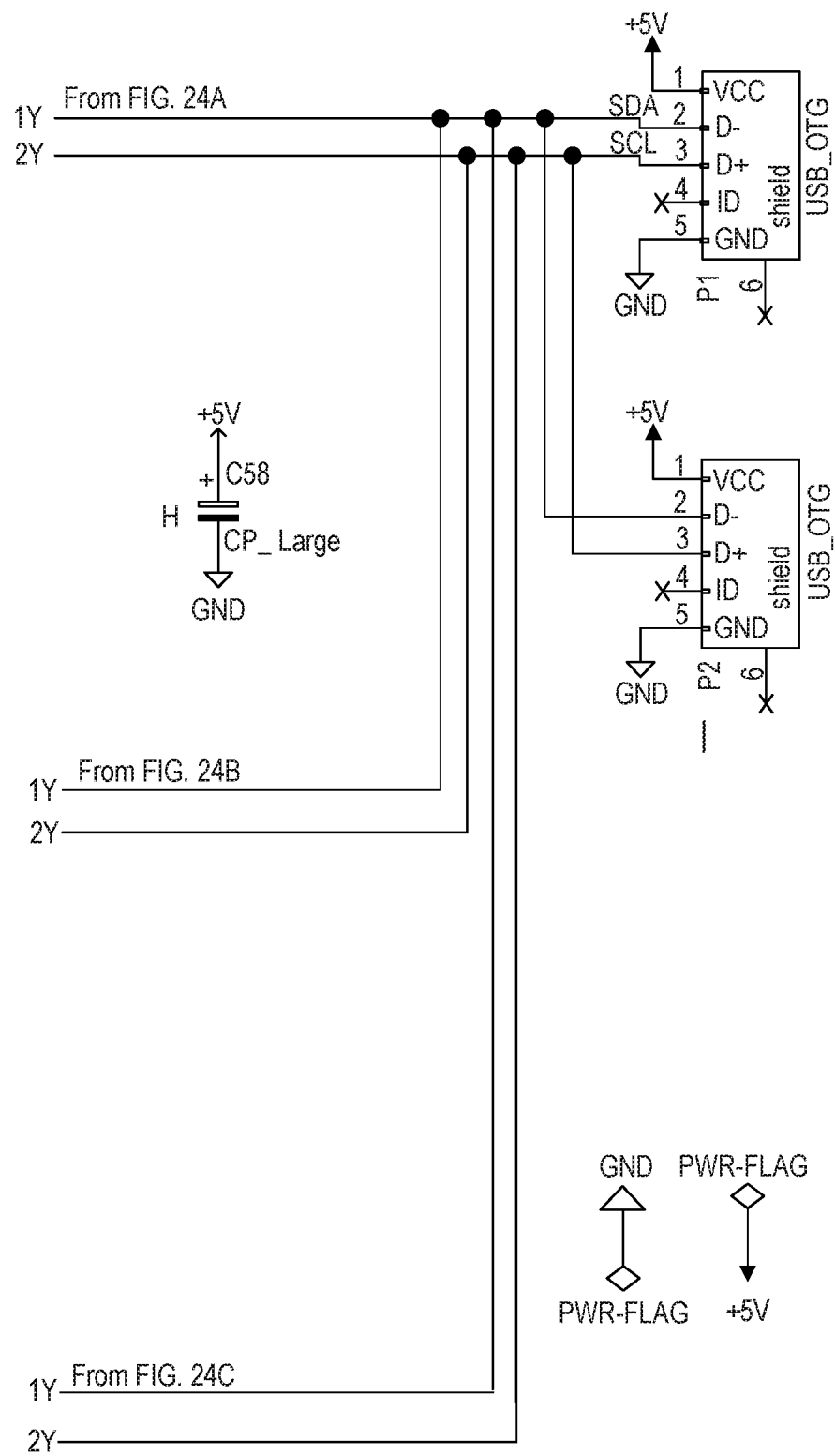
Figure 25:
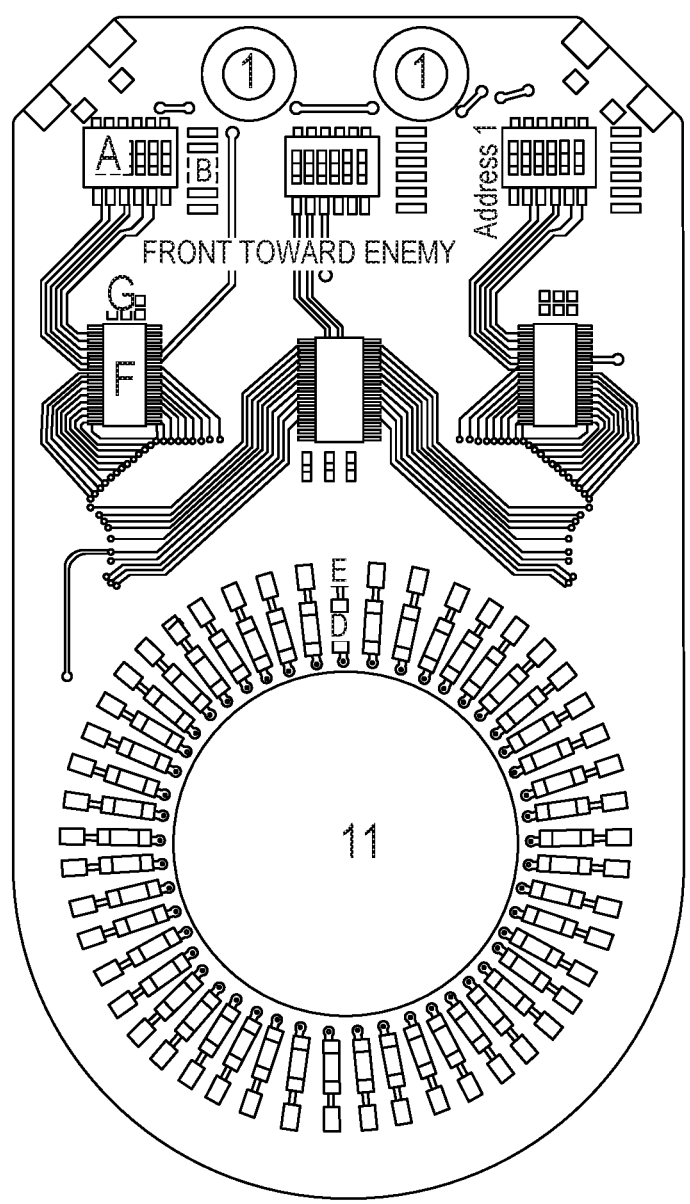
FIG. 25 is an illustration showing the front side of a circuit board/device which generates the varying levels of glaring light.
Figure 26:
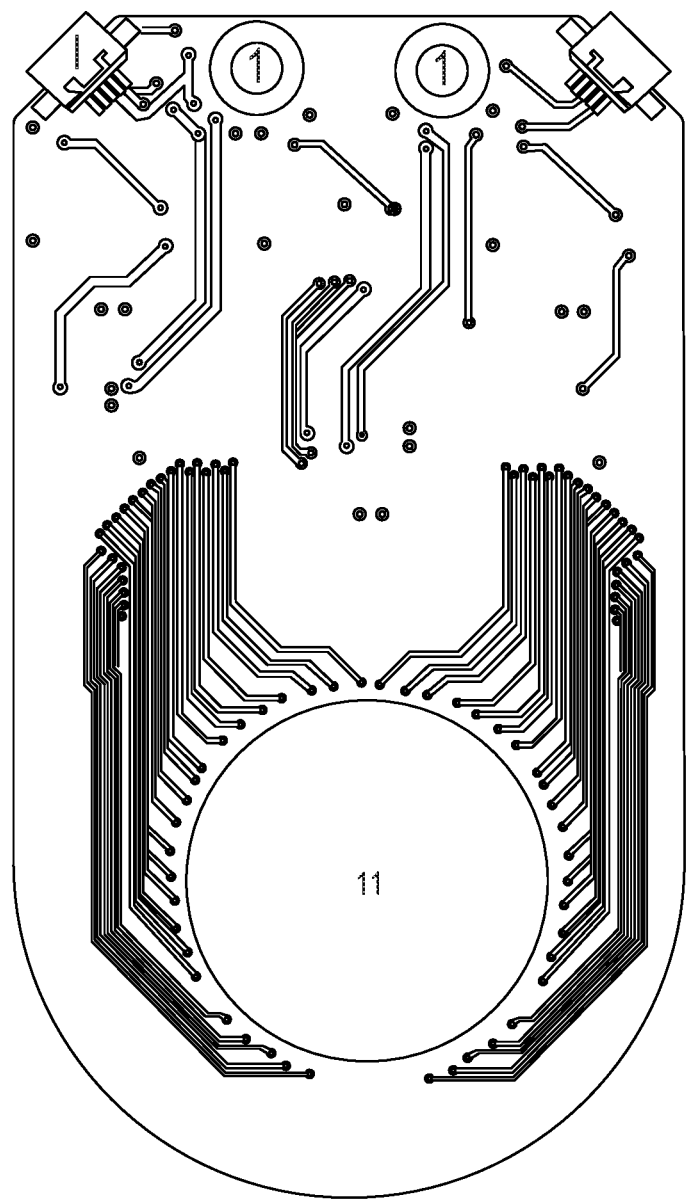
FIG. 26 is an illustration showing the back side of a circuit board/device which generates the varying levels of glaring light.
Figure 27:
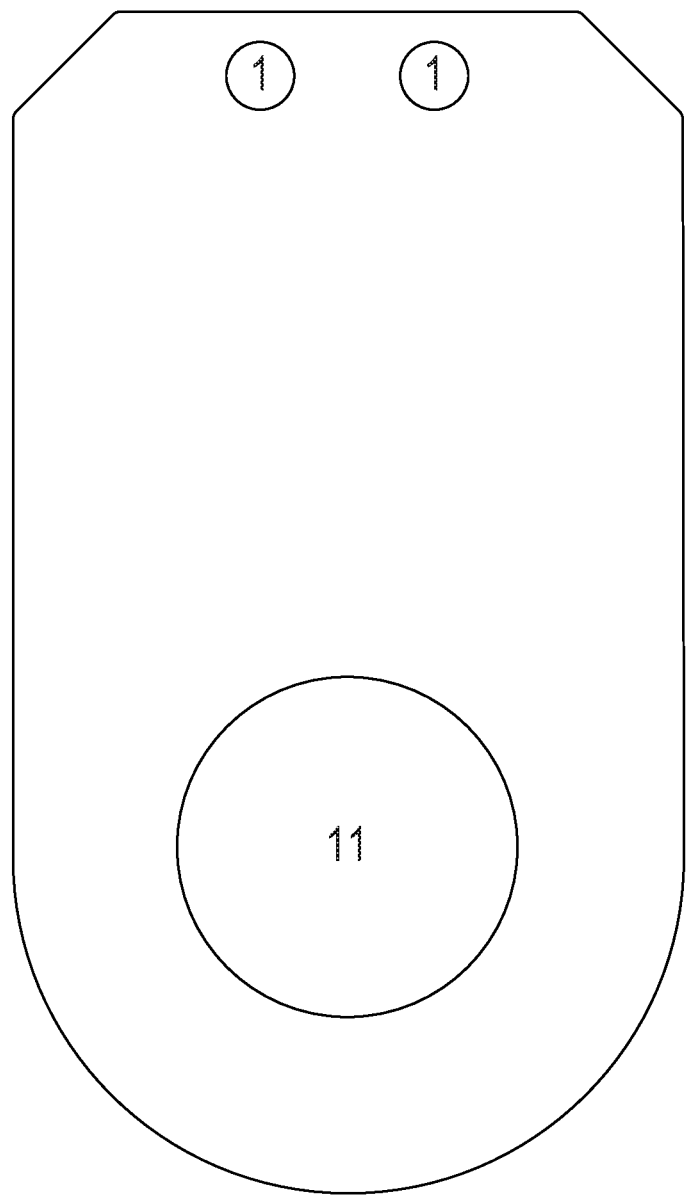
FIG. 27 is an illustration of the edge-cut layer of the circuit board/device which generates the varying levels of glaring light. Edge Cuts show routing path for creating the edge of the board and all holes that are not part of footprints or vias.
Figure 28:
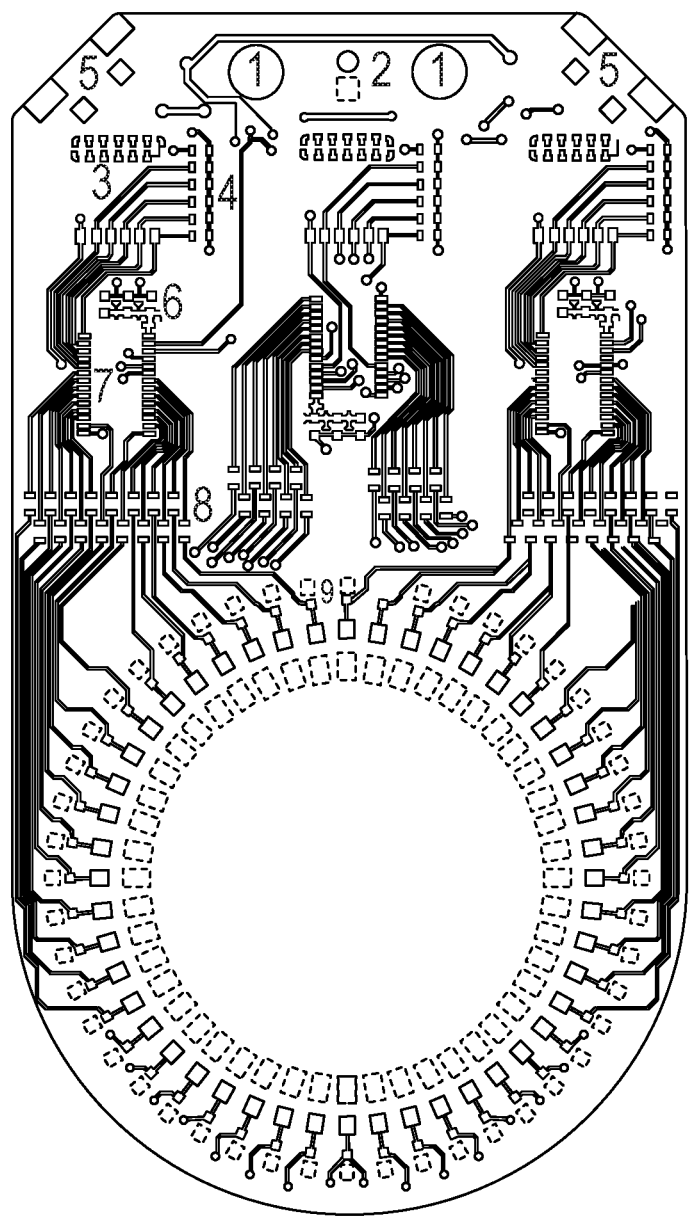
FIG. 28 is an illustration of front side copper layer of the circuit board/device which generates the varying levels of glaring light.
Figure 29:
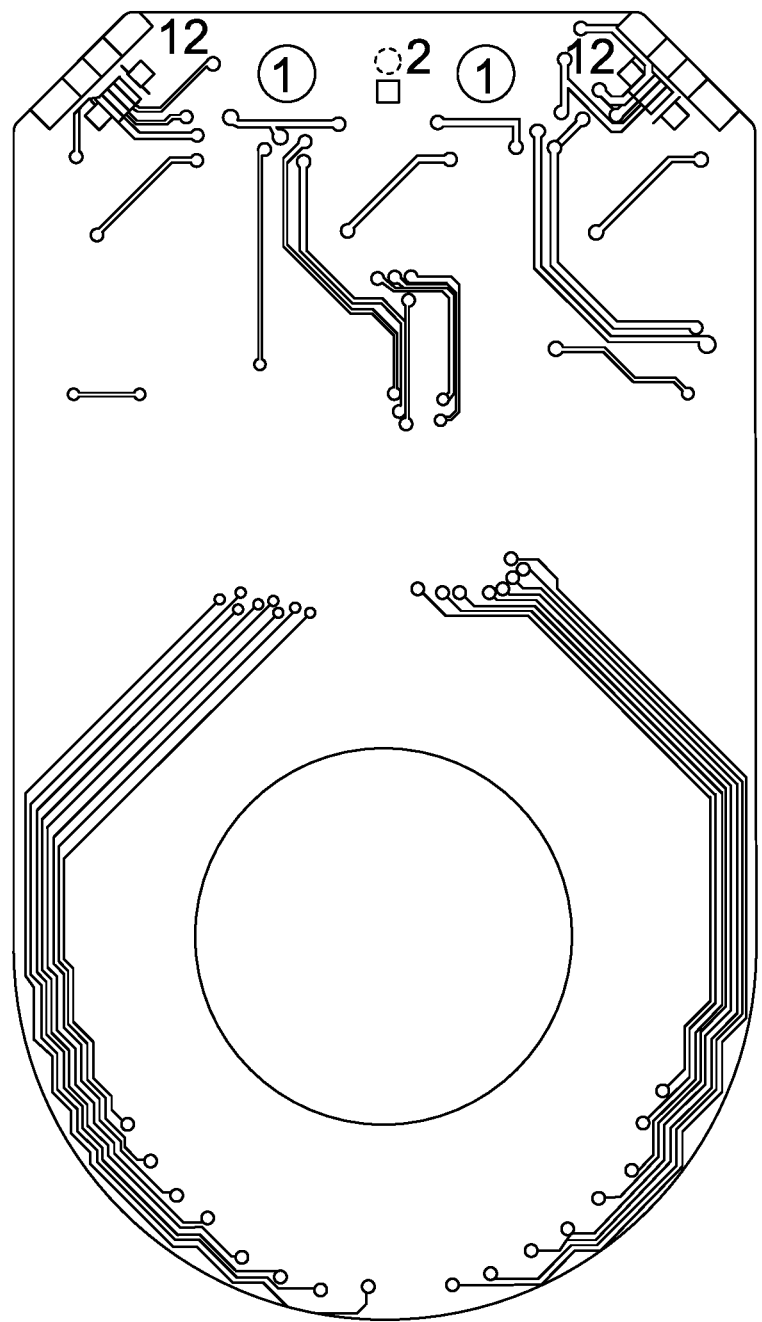
FIG. 29 is an illustration of the rear side copper layer of the circuit board/device which generates the varying levels of glaring light.

In other embodiments, a custom input device (consisting of a knob and arrays of buttons) is provided and sends emulated keyboard signals to the microcomputer via a microcontroller (FIGS. 6-10). The subject looks into the box through a ring of LEDs and sees a display at approximately 1-5 meters, preferably 1 meter, in distance. Inside of the box is the same perceptual size as the void in the center of the ring of LEDs. This allows for a correct viewing distance. The subject uses the control panel to select a task, glare intensity, and LCD backlight level (note: this step reflects an intended earlier application of performing demonstrations of the effects of glare, but this could easily be moved to an external computer, a set of external buttons, or other methods of having the experimenter/clinician perform the settings selection) (FIGS. 4-5). The backlight adjusts to the appropriate setting, the glare source turns on to the selected intensity, and the subject begins the task. The task can include any vision assessment task performed under glare conditions, so long as the stimulus can be presented on a monitor or similar display. For example, the task can be one of 4 tasks: (i) an acuity task; (ii) a contrast sensitivity task; (iii) a glare discomfort task; and (iv) a target detection task.

In an acuity task, the subject turns a knob to adjust the size of three rows of Landolt C optotypes that are in one of 8 orientations. This adjustment may increase or may decrease the size of the three rows. The subject presses a button when the middle row is just barely visible. The sizing and spacing of the three rows follows a standard Log MAR chart used in clinics around the world. With each adjustment, the orientation of the Landolt Cs randomizes. After the subject has indicated that they're near threshold (by pressing a button) the top and bottom rows disappear, a pair of chevrons appear above the left-most Landolt C, and the assessment switches to a forced choice task. The subject presses a button corresponding to the gap orientation of the indicated Landolt C, the chevrons move to right to the next position, the Landolt Cs randomize in orientation, and the subject repeats the process. If performance is high enough, the task is repeated but with the Landolt C size decreased. If performance is too low, the task is repeated but with the Landolt C size increased. If performance is significantly better than chance but not perfect, the task is considered finished, the glare source turns off, and the subject is returned to a menu. Significantly better than chance means at least 80% or 100% correct responses on a 5-trial 8-alternative forced choice task. Randomly guessing 4 or more correct responses would occur less than 0.1% of the time. Data is stored to the microcomputer for each response and is time-stamped.

In a contrast sensitivity task, the procedure is identical to the acuity task, but instead of the rows of Landolt C's being different sizes, they're different contrast levels (achieved by making them progressively lighter shades of gray on a white background)

In a glare discomfort task, after the glare source turns on, the subject selects a written description that best matches their subjective glare discomfort using a knob (and confirming with a button). Upon confirmation, the glare source turns off, the response is recorded, and the subject is returned to the task selection menu.

In a target detection task, after the glare source turns on, the subject is presented with a central fixation point for a randomized duration. After the duration has passed, the fixation point disappears and a circular target appears in one of 8 sections of a 3×3 grid (the central position being reserved for the fixation point). The subject presses one of 8 buttons on the input device which corresponds to their determination of the position of the target. The target disappears and then a randomized delay begins with the fixation point being present on the screen. If the response was correct, the contrast of the next target is lower to increase task difficulty. If the response was incorrect or there was not a response before a pre-defined timeout period, then the next target is of higher contrast for decreased difficulty. After a pre-defined number of incorrect responses, such as 3 trials with incorrect responses or no response, or if performance exceeds the contrast adjustment limits of the LCD display, the task exits, the glare source cuts off, and the subject is returned to the target detection screen. A larger number of trials before exit creates higher statistical confidence in a threshold estimation. A smaller number of trials is a shorter time-burden for the subject. Data is recorded to the microcomputer with each button press or missed response during this task. This approach could be used for performing any vision assessments under glare conditions, as long as the stimulus can be presented on a monitor or similar display.

The invention provides a method of testing visual glare in a human subject, the method comprising:
  (i) looking into a box through glare/light sources;
  (ii) visualizing a display at a measured distance;
  (iii) having a subject manipulate a control panel to select a task, glare intensity, and backlight level of said light sources;
  (iv) having a subject turn a knob to adjust size of rows of optotypes that are in one of 4 or more orientations to measure acuity;
  (v) having a subject turn a knob to adjust contrast levels of optotypes that are in one of 4 or more orientations to measure contrast sensitivity;
  (vi) having a subject turn a knob to select glare discomfort; and
  (vii) having a subject press one of 4 or more buttons on the input device that corresponds to position of a target.

The invention also provides a method for testing visual glare in a human subject using the glare testing device discussed herein comprising
  (i) having the subject look into the box through light/glare sources;
  (ii) having the subject visualize a display at a measured distance;
  (iii) having the subject manipulate the control panel to select the at least one task, glare intensity, and backlight level of said light sources;
  (iv) once the backlight is adjusted to appropriate setting and glare sources are turned on to selected intensity, having the subject begin the task;
  (v) once the subject finishes the task, storing data generated from results during the task to the microcomputer;
  (vi) analyzing the data to assess visual glare results.

In an embodiment, the at least one task is selected from the group consisting of (i) a visual acuity task, (ii) a contrast sensitivity task, (iii) a glare discomfort task, and (iv) a target detection task, or a combination of (i)-(iv).

In an embodiment, the (i) visual acuity task comprises having the subject turn a knob to adjust size of rows of optotypes that are in one of 4 or more orientations to measure acuity, the (ii) contrast sensitivity task comprises having the subject turn a knob to adjust contrast levels of optotypes that are in one of 4 or more orientations to measure contrast sensitivity, the (iii) glare discomfort task comprises after the glare sources turn on, having the subject turn a knob to select a written description that best matches the subject's glare discomfort, and the (iv) target detection task comprises after the glare sources turn on, having the subject matter press one of 4 or more buttons on the input device that corresponds to position of a target.

In an aspect, there's a small computer storing data to a micro-SD card which can be transferred over USB to external storage. In an aspect, the recorded data may also be communicated directly to a signal analyzer for analysis. A signal analyzer contains a processor and a memory coupled to the processor, the memory to store the data. The term "processor" encompasses all kinds of apparatus, devices, and machines for processing data, including by way of example a programmable microprocessor, a computer, a system on a chip, or multiple ones, or combinations, of the foregoing.

Processors include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a subject, embodiments of the subject matter described in this specification can be implemented on a computer having a display device, e.g., an LCD (liquid crystal display), LED (light emitting diode) display, OLED (organic light emitting diode) display, or electronic paper display, for displaying information to the subject and a keyboard and a pointing device, e.g., a mouse or a trackball, by which the subject can provide input to the computer. In some implementations, the subject interacts with the device using a series of buttons and a knob, wherein the knob emulates a mouse scroll-wheel and the buttons are keyboard key presses. In some implementations, a touch screen can be used to display information and receive input from a subject. In some implementations, the device can also be operated by a technician based on verbal or other feedback from a subject. Other kinds of devices can be used to provide for interaction with a subject as well; for example, feedback provided to the subject can be in any form of sensory feedback, e.g., visual feedback, auditory feedback, or tactile feedback; and input from the subject can be received in any form, including tactile input.

The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

In an embodiment, the subject inputs responses to the eye test/task using one or more of the input devices. The subject's responses are stored in the memory of the computer. In an aspect, the processor is configured to analyze the subject's response and to make a determination of the subject's vision results, i.e., assess reaction time on the target detection task, and hesitance on the discomfort, contrast sensitivity, and acuity measures. In an aspect, the method of vision testing can include the step of communicating the data to a device external to the computer for processing the data to determine the subject's vision test.

An embodiment includes a method for measuring the visual performance of a human subject, the method comprising analyzing the results of responses of the subject to at least one task selected from the group consisting of:
 visual acuity task;
 contrast sensitivity task;
 glare discomfort task; and
 target detection task.

In an aspect, the visual performance is measured under varying levels of veiling glare/glare intensity.

An embodiment includes a system for testing vision in a human subject, the system comprising:
 (a) a glare source providing various glare levels,
 (b) a control panel allowing for selection of a task, glare intensity, and backlight level of said light source,
 (c) a custom input device having knob and arrays of buttons which sends emulated keyboard signals to a microcomputer via a microcontroller,
 (d) a microcomputer having a means for recording results of at least one or more visual tasks of the human subject, means for storing the results, and means for transmitting said results to a signal analyzer, and
 (e) a signal analyzer having a memory for storing test results from one or more visual tasks of a human subject, means for receiving said test results, and a processor for processing said test results to calculate at least one aspect of the visual functioning of the human subject.

In an embodiment of the system, the one or more visual tasks is selected from the group consisting of (i) an acuity task, (ii) a contrast sensitivity task, (iii) a glare discomfort task, and (iv) a target detection task, or a combination of (i)-(iv).

Certain embodiments of the glare testing device and system are suitable for assessing glare under both mesopic and photopic vision (which is not incorporated into any identified commercially available equipment). Certain embodiments are directed to human visual performance testing. For example, the device and system can be used to assess speed and accuracy in target detection, a task that is uniquely important for deployed troops and is not part of any current glare assessments. The design of the glare source minimizes the impact of any lateral or vertical movement of the subject's head, preventing these postural adjustments from allowing one to decrease the impact of glare disability and improve performance threshold estimates.

In other embodiments, the glare testing device and system may evaluate the effect of glare on critical visual tasks under highly variable warfighter environmental conditions, which are not entirely dependent on corneal or crystalline lens opacities.

In other embodiments, the device and system may also be valuable to evaluate soldiers following exposure to directed energy weapons. Following directed energy exposure, soldiers may demonstrate transient or permanent visual disturbances or mild traumatic brain injury signs and symptoms, including complaints of glare, this device may allow quantification of the severity of glare which likely correlates with severity of injury.

In other embodiments, the device may identify pre-cataract glare related issues which would warrant IOL surgery or used to monitor typically slow-developing eye conditions, such as cataracts. This device may be useful in investigating the side-effects of refractive surgical procedures and identifying suitable candidates for different refractive surgeries. This device would be useful in identifying glare-related performance issues in drivers and pilots, both for civilian and military screening and licensing procedures. This device could also be useful for training (such as in flight simulators).

Preferred embodiments include a resolution of adjustment of glare intensity that is greater than any commercially available glare testers. Methods are provided for rapidly assessing threshold estimates with the visual acuity and contrast sensitivity measures This invention is believed to be the first intended for use in assessing glare effects during both photopic and mesopic vision. This invention is the first to incorporate a target detection task which measures reaction time under glaring conditions. The self-alignment method for the subject is not present in any existing glare testing equipment. The device achieves a high-intensity of glare localized near the eye in a homogenous field without the need for a diffuser, additional optics, or an integrating sphere.

In some embodiments, 4096 different glare levels allow for testing to assess performance and discomfort matching in a wide array of natural conditions. Instead of using static charts (like the VectorVision CV-1000™) or relying on the existing equipment of the clinic (like the Brightness Acuity Tester and the EpiGlare™), the invention generates vision testing stimuli in real-time with randomization to prevent cheating or learning effects. Instead of requiring an experimenter or clinician to manually record responses on paper or entering them into a computer, the invention allows for recordation of subject responses to files that can be easily read by software for later analysis. This device automatically turns the glare source on and off as needed, minimizing subject fatigue by reducing total light exposure. All subject responses with this device are recorded and time-stamped, making it possible to assess reaction time on the target detection task, and hesitance on the discomfort, contrast sensitivity, and acuity measures.

In other embodiments, a "demo" mode exists in which the user can turn a knob and step through any of the glare source brightness settings. At this point, a value is displayed on screen. Hardware is more than adequate for a minor software tweak that would allow a glare source to be adjusted to a threshold criteria while a stimulus remains static. This is an alternative embodiment to that where the testing method includes stimuli that are varied but the glare source intensity was set to a constant. Because the backlight intensity adjustment for the LCD display is performed using an external hardware device, rather than a software setting, it is possible to obtain a display well below photopic (i.e. daytime) vision levels and into the mesopic (i.e. twilight) range. By doing this with the backlight hardware, full software adjustment range is maintained so specified contrast of the stimuli can be varied independent of backlight intensity. This permits testing and comparing normal versus low-light visual performance, which may have military screening applications and potential clinical diagnostic use.

What is claimed is:

1. A glare testing device for testing visual glare on a human subject, the glare testing device comprising:
    an enclosure having two open ends spaced from each other;
    a display at one end of the enclosure;
    a glare source at the other end of the enclosure, the glare source having
        at least one circuit board having a plurality of light emitting diodes, the at least one circuit board is proximate to the other end of the enclosure, and
        a front plate having at least one opening passing therethrough configured for the human subject to look through towards the display; and
    a microcontroller in communication with the at least one circuit board and configured to activate the light emitting diodes to create a veiling glare, and
    wherein the only source of light internal to the enclosure are the display and the light emitting diodes.

2. The glare testing device of claim 1, wherein the enclosure is a tube.

3. The glare testing device of claim 2, wherein an inside of the enclosure is MATT black.

4. The glare testing device of claim 1, wherein the enclosure is a rectangular box.

5. The glare testing device of claim 1, wherein the glare source further includes a reference ring mounted in a reference ring enclosure, the reference ring enclosure includes a plurality of legs attached to the circuit board to space the reference ring from the circuit board along a line of sight between the opening in the front plate and the display.

6. The glare testing device of claim 1, further comprising a microcomputer mounted on the display end of the enclosure, the microcomputer configured to generate images to be shown on the display and control operation of the microcontroller.

7. The glare testing device of claim 1, wherein the plurality of light emitting diodes number at least 48, are arranged in a circle around an opening passing through the circuit board, and are facing the opening of the front plate.

8. The glare testing device of claim 1, wherein each of the light emitting diodes are independently controllable to allow for an angular location of the generated glare.

9. The glare testing device of claim 1, wherein the at least one circuit board includes two circuit boards arranged in parallel to each other and defining a passageway for the human subject to look through towards the display, and the light emitting diodes on each circuit board are face the opening of the front plate.

10. A glare testing device for testing visual glare on a human subject, the glare testing device comprising:
    a rectangular box having two open ends spaced from each other;
    a display at the first end of the box;
    a glare source at the second end of the box, the glare source having
        a front plate having an opening passing therethrough configured for the human subject to look through towards the display, and
        at least one circuit board having at least 24 light emitting diodes, each of the light emitting diodes is independently controllable and face the opening of the front plate, the at least one circuit board is proximate to the second end of the box;
    a microcontroller in communication with the at least one circuit board and configured to activate the light emitting diodes to create a veiling angular glare; and
    a microcomputer mounted on the display end of the enclosure, the microcomputer configured to generate images to be shown on the display and control operation of the microcontroller.

11. The glare testing device of claim 10, wherein the glare source further includes a reference ring mounted in a reference ring enclosure, the reference ring enclosure includes a plurality of legs attached to the circuit board to space the reference ring from the circuit board.

12. The glare testing device of claim 10, wherein the front plate and the circuit board each have a second opening passing therethrough aligned with other, the circuit board including additional light emitting diodes spaced around the second opening and face the second opening of the front plate.

* * * * *